(12) United States Patent
DeMarini et al.

(10) Patent No.: US 9,399,021 B2
(45) Date of Patent: *Jul. 26, 2016

(54) PHARMACEUTICAL COMPOSITION

(71) Applicant: Novartis AG, Basel (CH)

(72) Inventors: Douglas J. DeMarini, Collegeville, PA (US); Francisco Henriquez, Collegeville, PA (US); Ngocdiep T. Le, Collegeville, PA (US); Lihong Wang, Collegeville, PA (US)

(73) Assignee: Novartis AG, Basel (CH)

( * ) Notice: Subject to any disclaimer, the term of this patent is extended or adjusted under 35 U.S.C. 154(b) by 321 days.

This patent is subject to a terminal disclaimer.

(21) Appl. No.: 14/103,092

(22) Filed: Dec. 11, 2013

(65) Prior Publication Data

US 2014/0154316 A1 Jun. 5, 2014

Related U.S. Application Data

(63) Continuation of application No. 14/044,139, filed on Oct. 2, 2013, which is a continuation of application No. 13/330,949, filed on Dec. 20, 2011, now Pat. No. 8,580,304.

(60) Provisional application No. 61/424,967, filed on Dec. 20, 2010.

(51) Int. Cl.
| | |
|---|---|
| *A61K 9/28* | (2006.01) |
| *A61K 31/519* | (2006.01) |
| *A61K 9/20* | (2006.01) |
| *A61J 3/06* | (2006.01) |
| *A61J 3/10* | (2006.01) |
| *C07D 471/04* | (2006.01) |

(52) U.S. Cl.
CPC ............... *A61K 9/2059* (2013.01); *A61J 3/06* (2013.01); *A61J 3/10* (2013.01); *A61K 9/2009* (2013.01); *A61K 9/2018* (2013.01); *A61K 9/2054* (2013.01); *A61K 9/2095* (2013.01); *A61K 9/2813* (2013.01); *A61K 31/519* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 5,342,947 A | 8/1994 | Lackey et al. | |
| 5,491,237 A | 2/1996 | Fang et al. | |
| 5,559,235 A | 9/1996 | Luzzlo et al. | |
| 5,681,835 A | 10/1997 | Wilson | |
| 5,877,219 A | 3/1999 | Wilson | |
| 6,063,923 A | 5/2000 | Fang et al. | |
| 6,207,716 B1 | 3/2001 | Wilson | |
| 6,268,391 B1 | 7/2001 | Dickerson et al. | |
| 7,378,423 B2 * | 5/2008 | Kawasaki et al. ......... | 514/264.1 |
| 2006/0014768 A1 | 1/2006 | Kawasaki et al. | |
| 2008/0254131 A1 | 10/2008 | Vandse | |

FOREIGN PATENT DOCUMENTS

| | | |
|---|---|---|
| WO | 02/094824 | 11/2002 |
| WO | WO2005/121142 | 12/2005 |
| WO | WO2008/098104 | 8/2008 |
| WO | WO2008/136843 | 11/2008 |
| WO | WO2011/038082 | 3/2011 |
| WO | WO2011/038085 | 3/2011 |
| WO | WO2011/038380 | 3/2011 |
| WO | WO2011/047238 | 4/2011 |
| WO | WO2011/062930 | 5/2011 |
| WO | WO2012/027438 | 3/2012 |

OTHER PUBLICATIONS

ClinicalTrials.gov, Study 1 of 24, GSK1120212, Solid Tumors or Lymphoma, May 28, 2008.
ClinicalTrials.gov, Study 2 of 24, GSK1120212, Japanese Students with Solid Tumors, Jan. 22, 2011.
ClinicalTrials.gov, Study 3 of 24, GSK2118436 & GSK 1120212, Safety, Pharmacokinets, Feb. 12, 2010.
ClinicalTrials.gov, Study 4 of 24, GSK1120212, Everolimus in Cancer Subjects, Aug. 6, 2009.
ClinicalTrials.gov, Study 5 of 24, GSK1120212, Comb Therapy Advanced Solid Tumors, Nov. 18, 2010.
ClinicalTrials.gov, Study 6 of 24, GSK1120212, Absolute Bioavailability, Aug. 11, 2011.
ClinicalTrials.gov, Study 7 of 24, GSK1120212, Surg. Resectable Oral Cavity Squamous Cell Cancer, Mar. 12, 2012.
ClinicalTrials.gov, Study 8 of 24, GSK1120212, Safety, PK and PD of BKM120, Jun. 17, 2010.
ClinicalTrials.gov, Study 9 of 24, GSK1120212, Open-label Study Docetaxel in Stage IV, May 19, 2011.
ClinicalTrials.gov, Study 10 of 24, GSK1120212, Safety, PK of AKT and MEK Combination, Apr. 22, 2010.
ClinicalTrials.gov, Study 11 of 24, GSK1120212, Open-label Study Subjects with Solid Tumors, Jun. 9, 2011.
ClinicalTrials.gov, Study 12 of 24, GSK1120212, Food-Effect Study, Jun. 9, 2011.
ClinicalTrials.gov, Study 13 of 24, GSK1120212, Open-label Study Relapsed or Refractory Leukemias, Jun. 12, 2009.
ClinicalTrials.gov, Study 14 of 24, GSK1120212, Triple Negative Breast Cancer Kinome Response , Oct. 13, 2011.
ClinicalTrials.gov, Study 15 of 24, GSK1120212, Advanced Metastatic BRAF Mutation-positive Melanoma, Nov. 18 2010.

(Continued)

*Primary Examiner* — Tigabu Kassa
(74) *Attorney, Agent, or Firm* — Gregory Ferraro

(57) ABSTRACT

Disclosed are novel pharmaceutical compositions containing N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, methods of using the compositions in therapy and processes for preparing the same.

17 Claims, 2 Drawing Sheets

(56) References Cited

OTHER PUBLICATIONS

ClinicalTrials.gov, Study 16 of 24, GSK1120212, Safety Study, comb. With Docetaxel, etc., Aug. 30, 2010.
ClinicalTrials.gov, Study 17 of 24, GSK1120212, Rollover Study, Feb. 3, 2011.
ClinicalTrials.gov, Study 18 of 24, GSK1120212, BRAK Mutation-positive Melanoma prev. treated with or without BRAF Inhibitor, Nov. 25, 2009.
ClinicalTrials.gov, Study 19 of 24, GSK1120212, Combination Study with Gemcitabine in Subjects with Solid tumors, Dec. 10, 2009.
ClinicalTrials.gov, Study 20 of 24, GSK1120212, Comb. Therapy with Pazopanib Solid tumors with Adv Thyroid Cancer, Aug. 23, 2011.
ClinicalTrials.gov, Study 21 of 24, GSK1120212, Plus Gemcitabine vs Placebo Plus Gemcitabine in Metastatic Pancreatic Cancer, Aug. 30, 2010.
ClinicalTrials.gov, Study 22 of 24, GSK1120212, Multiple Myeloma or Solid Tumor cancers, Oct. 13, 2011.
ClinicalTrials.gov, Study 23 of 24, GSK1120212, Efficacy & Safety Study Uveal Melanoma, Mar. 18, 2010.
ClinicalTrials.gov, Study 24 of 24, GSK1120212, Rollover Study BRAK Mutation-Positive Tumors, Oct. 21, 2010.
Einzig, et al., *Proc. Sem. Soc. Clin. Oncology*, 20:46 (1996).
Forastire, et al., *Sem. Oncology*, 20:56 (1990).
Green, et al., *Cancer Treatment Review*, 26(4):269-286 (2000).
Holmes, et al., *Journal Nat'l Cancer Institute*, 83:1797 (1991).
Jackson, et al., *International Journal of Biochemistry and Cell Biology*, 29(7):935-938 (1997).
Kath et al., *Expert Opinion on Therapeutic Patents*, 10(6):803-818 (2000).
Kearns, et al., *Seminars in Oncology*, 3(6):16-23 (1995).
Kitada, et al., *Antisense Research Development*, 4:71-79 (1994).
Lackey, et al., *Bioorganic and Medicinal Chemistry Letters*, 10:223-226 (2000).
Leder, et al., *Cancer Cell*, 9:425 (2006).
Markman, et al., *Yale Journal of Biology & Medicine*, 64:583 (1991).
Marks, et al., *Nature Biotechnology*, 25:84-90 (2007).
Martinez-Iacaci, et al., *International Journal of Cancer*, 88(1):44-52 (2000).
Massague, et al., *Cancer Surveys*, 27:41-64 (1996).
McGuire, et al., *Ann. Intern. Medicine*, 111:273 (1989).
Oliff, et al., *BioChem Biophys Acta*, 1423(3):19-30 (1999).
Pearce, et al., *Nature Reviews Molecular Cell Biology*, 11:9-22 (2010).
Philip, et al., *Cancer Treatment and Research*, 78:3-27 (1995).
Reilly, et al., *Cancer Research*, 60:3569-3576 (2000).
Richon, et al., *Proc. National Academy of Science USA*, 97(18):10014-10019 (2000).
Rosania, et al., *Expert Opinion on Therapeutic Patents*, 10(2):215-230 (2000).
Scharovsky, et al., *Journal of Biomedical Science*, 7(4):292-298 (2000).
Schreiber, et al., *Science*, 232:1250-1253 (1986).
Shawyer, et al., *DDT*, 2(2) 1997.
Sinh, et al., *Journal of Hematotherapy and Stem Cell Research*, 8(5):465-480 (1999).
Smithgall, et al., *Journal of Pharmacological and Toxicological Methods*, 34(3):125-132 (1995).
Vigushin, et al., *Anticancer Drugs*, 13(1):1-13 (2002).
Vinodhkumar, et al., *Biomedicine & Pharmacotherapy*, 62:85-93 (2008).
Wani, et al., *J. Am. Chem. Soc.*, 93:2325 (1971).
Waters, et al., *Journal of Clinical Oncology*, 18:1812-1823 (2000).
Williamson, et al., *The Journal of Allergy and Clinical Immunology*, 118(6):1369-1374 (2006).
Yammamoto, et al., *Journal of Biochemistry*, 126(5):799-803 (1999).
*Bertland European Journal of Medicinal Chemistry*, 45:2095-2116 (2010).
Bolen, et al., *Annual Review of Immunology*, 15:371-404 (1997).
Bouma, et al., *Journal of Antimicrobiology Chemotherapy*, 42(6):817-820 (1998).
*Breast Cancer Research*, 2(3):176-183 (2000).
Brekken, et al., *Cancer Research*, 60:5117-5124 (2000).
Brodt, et al., *Biochemical Pharmacology*, 60:1101-1107 (2000).
Bruns, et al., *Cancer Research*, 60:2926-2935 (2000).
Canman, et al., *Oncogene*, 17(25)3301-3308 (1998).
Chen, et al., *Cancer Research*, 58:1965-1971 (1998).
*Drugs of the Future*, 32(4):315-322 (2007).
Feling, et al., *Angew Chem Int Ed Engl*, 42(3):355-357 (2003).
Gottlicher, et al., *EMBO Journal*, 20(24):6969-6978 (2001).
Kingston, et al., *Studies in Organic Chemistry*, 26:219-235 (1986).
Kumar, et al., *J. Biol. Chem.*, 256:10435-10441 (1981).
Schiff, et al., *Nature*, 277:665-667 (1979).
Schiff, et al., *Proc. Natl. Acad. Sci. USA*, 77:1561-1565 (1980).
Woo, et al., *Nature*, 368:750 (1994).
Yen, et al., *Oncogene*, 19:3460-3469 (2000).
Zhong, et al., *Cancer Research*, 60(6):1541-1545 (2000).
Stenger, *Community Oncology*, 4:384-386 (2007).
Tennant, et al., *Nature Reviews Cancer*, 267 (2010).
Abraham, *Current Opinion in Immunology*, 8(3):412-418 (1996).
Adams, *Cancer Invest*, 22(2):304-311 (2004).
Ashby, *Current Opinion in Lipidology*, 9(2):99-102 (1998).
Balasubramanian, et al., *Cancer Letters*, 280:211-221 (2009).
Ball, el al., *Progress in Cell Cycle Research*, 3:125 (1997).
U.S. Appl. No. 08/977,217, filed Aug. 8, 2000, Besterman et al.

\* cited by examiner

PHARMACEUTICAL COMPOSITION

This application is a continuation of U.S. application Ser. No. 14/044,139 filed on 2 Oct. 2013, which is a continuation of U.S. application Ser. No. 13/330,949 filed on 20 Dec. 2011, now U.S. Pat. No. 8,580,304, which claims the benefit of U.S. Provisional Application No. 61/424,967 filed 20 Dec. 2010, which is incorporated herein in its entirety.

FIELD OF THE INVENTION

The present invention relates to solid oral pharmaceutical dosage forms, suitably tablets, suitably capsules, comprising N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, represented by the following formula (I) and hereinafter referred to as Compound A:

(Compound A)

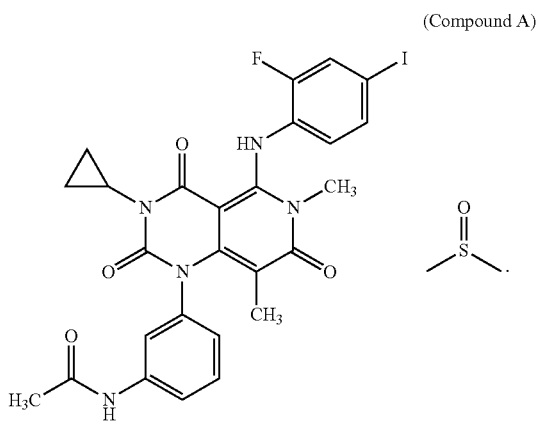

BACKGROUND OF THE INVENTION

N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, as the un-solvated compound (hereinafter Compound B) is a compound which is disclosed and claimed, along with pharmaceutically acceptable salts and solvates thereof, as being useful as an inhibitor of MEK activity, particularly in treatment of cancer, in International Application No. PCT/JP2005/011082, having an International filing date of Jun. 10, 2005; International Publication Number WO 2005/121142 and an International Publication date of Dec. 22, 2005, the entire disclosure of which is hereby incorporated by reference. Compound B is the compound of Example 4-1. Compound B can be prepared as described in International Application No. PCT/JP2005/011082. Compound B can be prepared as described in United States Patent Publication No. US 2006/0014768, Published Jan. 19, 2006, the entire disclosure of which is hereby incorporated by reference. Compound B is the compound of Example 4-1.

Suitably, Compound B is in the form of a dimethyl sulfoxide solvate, or Compound A as defined herein. Suitably, Compound B is in the form of a solvate selected from: hydrate, acetic acid, ethanol, nitromethane, chlorobenzene, 1-pentanol, isopropyl alcohol, ethylene glycol and 3-methyl-1-butanol. Solvates and salt forms can be prepared by one of skill in the art, for example from the description in International Application No. PCT/JP2005/011082 or United States Patent Publication No. US 2006/0014768. Compound A is prepared in Example 4-149 of United States Patent Publication No. US 2006/0014768.

Solid oral pharmaceutical dosage forms are popular and useful forms of medications for dispensing pharmaceutically active compounds. A variety of such forms are known, including tablets, capsules, pellets, lozenges, and powders.

However, the formulation of an acceptable solid oral pharmaceutical dosage form on a commercial scale is not straightforward. When administered in vivo, each pharmaceutical compound acts uniquely in regards to therapeutic drug levels. Further, pharmaceutically active compounds, particularly anti-neoplastic compounds, are often associated with undesirable side effects such as; toxicity (e.g. genotoxicity, teratogenicity) and undesirable physical or psychological manifestations. In addition to balancing the drug's unique chemical properties with those of the excipients, the drug must be administered at a specific amount that is sufficient to provide the desired therapeutic drug level but less than the amount that presents an unacceptable side effect profile, or within the therapeutic window for that particular drug. Moreover, the formulation and process of manufacture must be such as to provide an integral solid dosage form that maintains its integrity until used. The solid dosage form must also possess acceptable dissolution and disintegration properties so as to provide the desired profile in use. Pharmaceutically active compounds with low solubility and/or in solvate form can present particular challenges in preparing high quality solid dosage forms. These challenges include insufficient and inconsistent exposure upon in vivo administration and desolvation which releases unsolvated compound which can exhibit poor pharmacodynamic properties.

It would be desirable to provide Compound A in a solid oral pharmaceutical dosage form on a commercial scale with a desirable pharmacodynamic profile.

SUMMARY OF THE INVENTION

The present invention relates to solid oral pharmaceutical dosage forms, suitably tablets, suitably capsules, comprising a therapeutically effective amount of Compound A. The invention also relates to a process for making solid oral pharmaceutical dosage forms, suitably tablets, suitably capsules, comprising Compound A.

Another aspect of this invention relates to solid oral pharmaceutical dosage forms, suitably tablets, suitably capsules, comprising Compound A that are formulated using excipients, suitably the diluent component, that are substantially free of water, which as used herein and in the claims includes anhydrous versions of non-anhydrous excipients. Such solid oral pharmaceutical dosage forms exhibit improved properties. Such improved properties help to ensure safe and effective treatment.

Another aspect of this invention relates to a pharmaceutical tablet comprising a therapeutically effective amount of Compound A, wherein the tablet is prepared by compression of dry blend, suitably by direct compression or by dry granulation. Such pharmaceutical tablet exhibits improved properties. Such improved properties help to ensure safe and effective treatment. The invention also relates to a method of making direct compression and dry granulation pharmaceutical tablets comprising Compound A.

Another aspect of this invention relates to film coated oral pharmaceutical tablets comprising Compound A, suitably the film coat is an aqueous film coat composition comprising a film-forming polymer and water as a vehicle, suitably containing a pigment or colorant, suitably an iron oxide containing pigment or colorant. Such tablets exhibit improved properties. Such improved properties help to ensure safe and effective treatment.

Another aspect of this invention relates to solid oral pharmaceutical dosage forms, suitably tablets, suitably capsules, comprising Compound A in an amount selected from: 0.5, 1 and 2 mg, by weight of Compound B. Such solid oral pharmaceutical dosage forms exhibit improved properties. Such improved properties help to ensure safe and effective treatment.

Another aspect of this invention relates to solid oral pharmaceutical dosage forms, suitably tablets, suitably capsules, containing Compound A in which Compound A is in micronized form. Such solid oral pharmaceutical dosage forms exhibit improved properties. Such improved properties help to ensure safe and effective treatment.

Another aspect of this invention relates to solid oral pharmaceutical dosage forms, suitably tablets, suitably capsules, containing Compound A in which at least 50% of the Compound A particles have a particle size of 30 micron or less, suitably at least 50% of the Compound A particles have a particle size of 10 micron or less, suitably at least 50% of the Compound A particles have a particle size of 5 micron or less. Such solid oral pharmaceutical dosage forms exhibit improved properties. Such improved properties help to ensure safe and effective treatment.

Another aspect of the this invention relates to solid oral pharmaceutical dosage forms, suitably tablets, suitably capsules, containing Compound A in which the amount of unsolvated compound (or Compound B as used herein) does not exceed about 20%, suitably the amount of unsolvated compound does not exceed about 15%, suitably the amount of unsolvated compound does not exceed about 10%, suitably the amount of unsolvated compound does not exceed about 5%, suitably the amount of unsolvated compound does not exceed about 2%. Such solid oral pharmaceutical dosage forms exhibit improved properties. Such improved properties help to ensure safe and effective treatment.

Another aspect of this invention relates to a method of treating cancer in a mammal, including a human, which method comprises administering to a subject in need thereof a solid oral pharmaceutical dosage form, suitably a tablet, suitably a capsule, of the present invention that contains an amount of Compound A selected from: 0.5, 1 and 2 mg, by weight of Compound B.

Another aspect of this invention relates to a method of inhibiting MEK, in a human, which method comprises administering to a subject in need thereof a solid oral pharmaceutical dosage form, suitably a tablet, suitably a capsule, of the present invention that contains an amount of Compound A selected from: 0.5, 1 and 2 mg, by weight of Compound B.

Also included in the present invention are methods of co-administering a solid oral pharmaceutical dosage form of the present invention with further active ingredients, suitably the further active ingredients are anti-neoplastic agents.

DETAILED DESCRIPTION OF THE INVENTION

Figure 1:
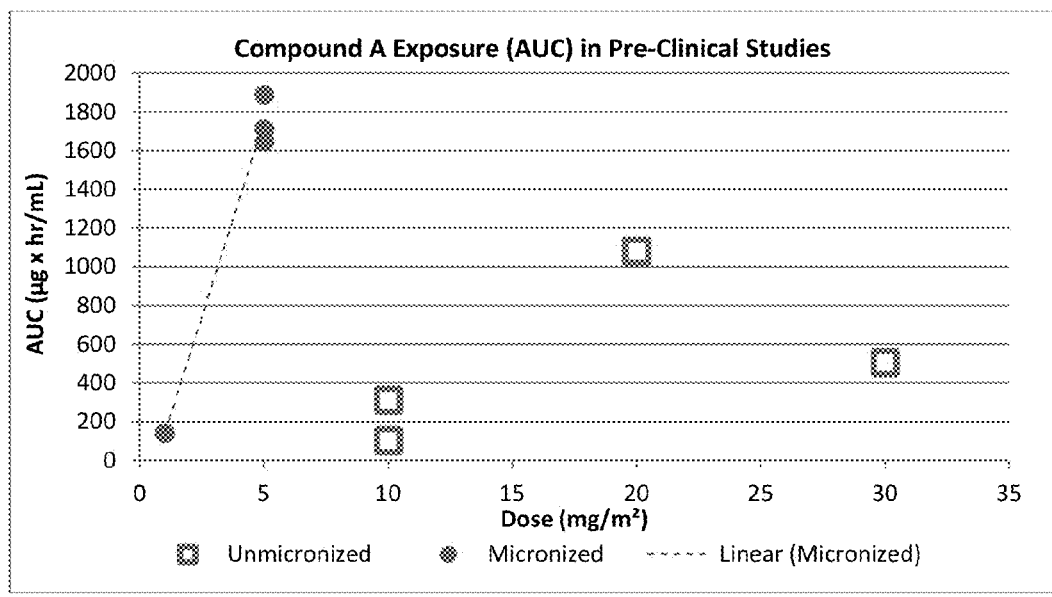
FIG. 1 depicts the exposure (AUC) data for Compound A in pre-clinical studies in a rat model.

Compound A presents the formulator with unique concerns when attempting to formulate this compound into a suitable solid oral pharmaceutical dosage form, suitably a tablet, suitably a capsule, within the therapeutic window for Compound A, particularly on a commercial scale. Such concerns include but are not limited to; the tendency of the compound to revert to an insoluble desolvated form when exposed to moisture during the formulation process, slow dissolution of the compound from solid dosage forms, and that Compound A can suffer from photo-instability.

Significant realization of these concerns will have an adverse effect on the in vivo administration of Compound A.

It would be desirable to provide Compound A in tablet form on a commercial scale, since tablets tend to provide greater accuracy of dosage, convenient administration, increased durability and stability during storage, shorter production time, and economy and efficiency in storage, packaging and shipping. Unfortunately, photo-instability of Compound A becomes a potential concern in tablet forms.

In one embodiment, the present invention is directed to solid oral pharmaceutical dosage forms that contain Compound A, suitably the solid dosage form is a tablet, suitably the solid dosage form is a capsule, suitably these solid dosage forms are produced on a commercial scale.

It has been found that Compound A can suffer from photo-instability. The potential for unacceptable levels of photo-degradation is of particular importance since photo-catalyzed degradation products may be potentially toxic.

It has now been discovered that Compound A tablets that are coated with an aqueous colored film coat, suitably an iron oxide containing colored film coat, for example Opadry® yellow or pink, exhibit improved photo-stability. This improved stability leads to a reduction in the levels of photo-catalyzed degradation products forming upon light exposure. Such improved stability helps to ensure safe and effective treatment.

In one embodiment, the present invention is directed to tablets containing Compound A that are coated with an aqueous colored film coat. Suitably these tablet forms are produced on a commercial scale. These tablet forms help provide safe and effective treatment.

It has been found that Compound A can cause toxic effects when administered in high doses. It has been discovered that Compound A, when administered in an amount selected from about 0.5 mg, 1 mg and 2 mg, based on the amount of Compound B, is sufficient to provide the desired therapeutic drug level but less than the amount that presents an unacceptable side effect profile, or within the therapeutic window for Compound A.

In one embodiment, the present invention is directed to tablets containing Compound A in an amount selected from: about 0.5 mg, 1 mg and 2 mg based on the amount of Compound B. These tablet strengths help provide safe and effective treatment.

It has been found that Compound A can undergo desolvation during handling and formulation resulting in unsolvated Compound B being formed. Compound B is much less soluble than Compound A, which negatively impacts its pharmacodynamics when released from a pharmaceutical composition. It has been found that pharmaceutical formulations, suitably tablets, suitably capsules, in which the amount of desolvated Compound B does not exceed 20%, suitably does not exceed 15%, suitably does not exceed 10%, suitably does not exceed 5%, suitably does not exceed 2%, when compared to Compound A, provide an acceptable release/pharmacodynamic profile.

In one embodiment, the present invention is directed to tablets containing Compound B in an amount that does not exceed about 20%, suitably about 15%, suitably about 10%, suitably about 5%, suitably about 2% of the amount of Compound A. Such tablets help provide safe and effective treatment.

It has been found that Compound A can exhibit poor exposure and absorption upon in vivo administration. It has been found that pharmaceutical formulations, suitably tablets, suitably capsules, in which Compound A is micronized, suitably where at least 50% or the particles of Compound A are 30 micron or less, suitably at least 50% of the particles of Compound A are 10 micron or less, suitably at least 50% of the particles of Compound A are 5 micron or less, provide an acceptable exposure/absorption profile.

In one embodiment, the present invention is directed to tablets containing Compound A in micronized form, suitably where at least 50% of the particles of Compound A are 30 micron or less, suitably at least 50% of the particles of Compound A are 10 micron or less, suitably at least 50% of the particles of Compound A are 5 micron or less. Such tablets help provide safe and effective treatment.

As used herein, the term "improved properties" and derivatives thereof, contemplates several advantages to the pharmacokinetic profile of the in vivo release of Compound A from a formulation, suitably a solid oral pharmaceutical dosage form, suitably a capsule, suitably a tablet, that utilizes an aspect of the present invention when compared to a formulation that does not utilize that aspect of the present invention, suitably the formulation is produced on a commercial scale. Examples of improved properties include: increased oral bioavailability, improved physical and chemical stability, improved photo-stability, a consistent pharmacokinetic profile, an improved pharmacokinetic profile and a consistent dissolution rate.

As used herein, the term "drug" or "active ingredient" and derivatives thereof, unless otherwise defined, means Compound A or N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide.

As used herein, the term "Compound B" and derivatives thereof, means N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, as the free or unsalted and unsolvated compound. Compound B also refers to the amount of free or unsalted and unsolvated compound in an amount of Compound A.

By the term "commercial scale" and derivatives thereof, as used herein is meant, preparation of a batch scale greater than about 20 kg of direct compression mix, suitably greater than 50 kg, suitably greater than 75 kg or a batch size suitable to prepare at least about 50,000 solid oral pharmaceutical dosage forms, suitably tablets, suitably capsules, suitably at least 75,000 solid oral pharmaceutical dosage forms, suitably tablets, suitably capsules, suitably at least 100,000 solid oral pharmaceutical dosage forms, suitably tablets, suitably capsules.

The term "effective amount" and derivatives thereof, means that amount of a drug or active ingredient that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "formulation" and derivatives thereof, unless otherwise defined refers to solid oral pharmaceutical dosage forms, suitably tablets, suitably capsules, of the invention that contain Compound A.

By the term "co-administration" as used herein is meant either simultaneous administration or any manner of separate sequential administration of a solid oral pharmaceutical dosage form containing Compound A, and a further active agent or agents, known to be useful in the treatment of cancer, including chemotherapy and radiation treatment. The term further active agent or agents, as used herein, includes any compound or therapeutic agent known to or that demonstrates advantageous properties when administered to a patient in need of treatment for cancer. As used herein, "further active agent or agents" is used interchangeably with further anti-neoplastic agent or agents. Preferably, if the administration is not simultaneous, the compounds are administered in a close time proximity to each other. Furthermore, it does not matter if the compounds are administered in the same dosage form, e.g. one compound may be administered by injection and another compound may be administered orally. Suitably, the "co-administration" will consist essentially of a solid oral pharmaceutical dosage form containing compound A and a second pharmaceutical dosage form containing a further active agent. Suitably, the "co-administration" will consist essentially of a solid oral pharmaceutical dosage form containing compound A, a second pharmaceutical dosage form containing a further active agent, and a third pharmaceutical dosage form containing another further active agent.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; cell cycle signaling inhibitors; proteasome inhibitors; and inhibitors of cancer metabolism.

Examples of a further active agent or agents (anti-neoplastic agent) for use in combination or co-administered with a presently invented pharmaceutical dosage form, are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, equation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of Streptomyces verticillus, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl] methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of Formula A following, including the racemic mixture (R,S) form as well as the R and S enantiomers:

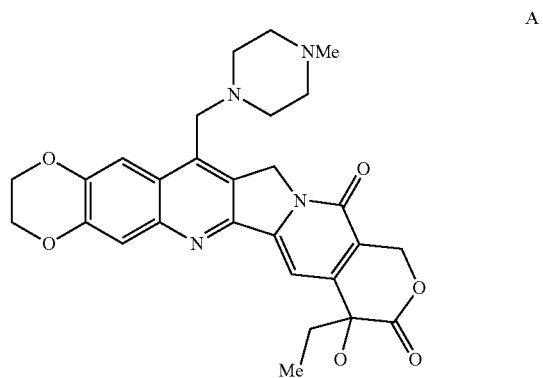 [SMILES: CCC1(O)C(=O)OCc2c1cc1n(c2=O)Cc2c-1nc1cc3c(cc1c2CN1CCN(C)CC1)OCCO3]

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphotidylinositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and antisense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, P13-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, PDK1 and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; Pearce, L. R et al. Nature Reviews Molecular Cell Biology (2010) 11, 9-22. and Martinez-Iacaci, L., et al, Int. J. Cancer (2000), 88(1), 44-52.

Suitably, the pharmaceutically active compound of the invention is used in combination with a B-Raf inhibitor. Suitably, N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt thereof, which is disclosed and claimed, in International Application No. PCT/US2009/042682, having an International filing date of May 4, 2009, the entire disclosure of which is hereby incorporated by reference. N-{3-[5-(2-Amino-4-pyrimidinyl)-2-(1,1-dimethylethyl)-1,3-thiazol-4-yl]-2-fluorophenyl}-2,6-difluorobenzenesulfonamide can be prepared as described in International Application No. PCT/US2009/042682.

Suitably, the pharmaceutically active compound of the invention is used in combination with an Akt inhibitor. Suitably, N-{(1S)-2-amino-1-[(3,4-difluorophenyl)methyl]ethyl}-5-chloro-4-(4-chloro-1-methyl-1H-pyrazol-5-yl)-2-furancarboxamide or a pharmaceutically acceptable salt thereof, which is disclosed and claimed in International Application No. PCT/US2008/053269, having an International filing date of Feb. 7, 2008; International Publication Number WO 2008/098104 and an International Publication date of Aug. 14, 2008, the entire disclosure of which is hereby incorporated by reference. N-{(1S)-2-amino-1-[(3,4-difluorophenyl)methyl]ethyl}-5-chloro-4-(4-chloro-1-methyl-1H-pyrazol-5-yl)-2-furancarboxamide is the compound of example 224 and can be prepared as described in International Application No. PCT/US2008/053269.

Suitably, the pharmaceutically active compound of the invention is used in combination with an Akt inhibitor. Suitably, N-{(1S)-2-amino-1-[(3-fluorophenyl)methyl]ethyl}-5-chloro-4-(4-chloro-1-methyl-1H-pyrazol-5-yl)-2-thiophenecarboxamide or a pharmaceutically acceptable salt thereof, which is disclosed and claimed in International Application No. PCT/US2008/053269, having an International filing date of Feb. 7, 2008; International Publication Number WO 2008/098104 and an International Publication date of Aug. 14, 2008, the entire disclosure of which is hereby incorporated by reference. N-{(1S)-2-amino-1-[(3-fluorophenyl)methyl]ethyl}-5-chloro-4-(4-chloro-1-methyl-1H-pyrazol-5-yl)-2-thiophenecarboxamide is the compound of example 96 and can be prepared as described in International Application No. PCT/US2008/053269. Suitably, N-{(1S)-2-amino-1-[(3-fluorophenyl)methyl]ethyl}-5-chloro-4-(4-chloro-1-methyl-1H-pyrazol-5-yl)-2-thiophenecarboxamide is in the form of a hydrochloride salt. The salt form can be prepared by one of skill in the art from the description in International Application No. PCT/US2010/022323, having an International filing date of Jan. 28, 2010.

Inhibitors of Phosphotidylinositol-3 Kinase family members including blockers of PI3-kinase, ATM, DNA-PK, and Ku may also be useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also of interest in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kniases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also be useful in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alpha beta$_3$) that will inhibit angiogenesis; endostatin and angiostatin (non-RTK) may also prove useful in combination with the disclosed compounds. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of Formula (I). There are a number of immunologic strategies to generate an immune response. These strategies are generally in the realm of tumor vaccinations. The efficacy of immunologic approaches may be greatly enhanced through combined inhibition of signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230. Further, p21WAF1/CIP1 has been described as a potent and universal inhibitor of cyclin-dependent kinases (Cdks) (Ball et al., *Progress in Cell Cycle Res.*, 3: 125 (1997)). Compounds that are known to induce expression of p21WAF1/CIP1 have been implicated in the suppression of cell proliferation and as having tumor suppressing activity (Richon et al., *Proc. Nat Acad. Sci. U.S.A.* 97(18): 10014-10019 (2000)), and are included as cell cycle signaling inhibitors. Histone deacetylase (HDAC) inhibitors are implicated in the transcriptional activation of p21WAF1/CIP1 (Vigushin et al., *Anticancer Drugs*, 13(1): 1-13 (January 2002)), and are suitable cell cycle signaling inhibitors for use herein. Examples of such HDAC inhibitors include:

1. Vorinostat, including pharmaceutically acceptable salts thereof. Marks et al., *Nature Biotechnology* 25, 84 to 90 (2007); Stenger, *Community Oncology* 4, 384-386 (2007).

Vorinostat has the following chemical structure and name:

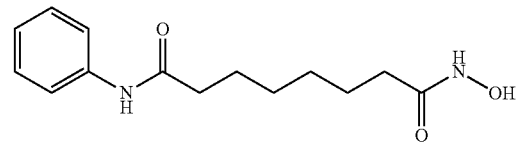 [SMILES: O=C(CCCCCCC(=O)Nc1ccccc1)NO]

N-hydroxy-N'-phenyl-octanediamide

2. Romidepsin, including pharmaceutically acceptable salts thereof.

Vinodhkumar et al., *Biomedicine & Pharmacotherapy* 62 (2008) 85-93.

Romidepsin, has the following chemical structure and name:

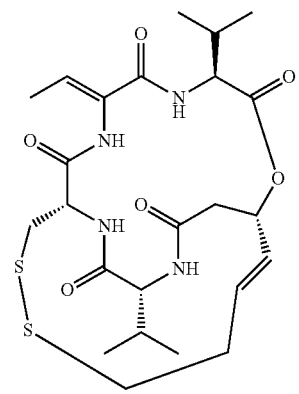 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]

(1S,4S,7Z,10S,16E,21R)-7-ethylidene-4,21-di(propan-2-yl)-2-oxa-12,13-dithia-5,8,20,23-tetrazabicyclo[8.7.6]tricos-16-ene-3,6,9,19,22-pentone 3. Panobinostat, including pharmaceutically acceptable salts thereof. *Drugs of the Future* 32(4): 315-322 (2007).

Panobinostat, has the following chemical structure and name:

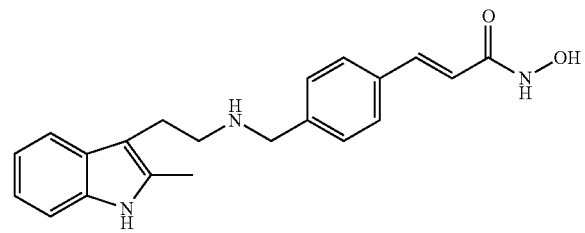 [SMILES: Cc1[nH]c2ccccc2c1CCNCc1ccc(/C=C/C(=O)NO)cc1]

(2E)-N-hydroxy-3-[4-({[2-(2-methyl-1H-indol-3-yl)ethyl]amino}methyl)phenyl]acrylamide 4. Valproic acid, including pharmaceutically acceptable salts thereof. Gottlicher, et al., *EMBO J.* 20(24): 6969-6978 (2001).

Valproic acid, has the following chemical structure and name:

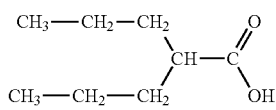

2-propylpentanoic acid

5. Mocetinostat (MGCD0103), including pharmaceutically acceptable salts thereof. Balasubramanian et al., *Cancer Letters* 280: 211-221 (2009).

Mocetinostat, has the following chemical structure and name:

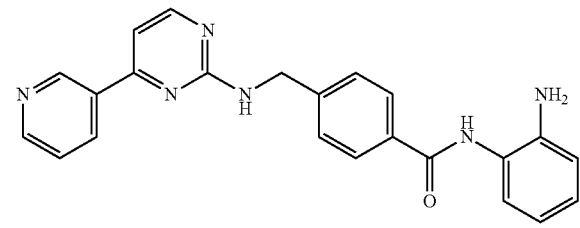 [SMILES: Nc1ccccc1NC(=O)c1ccc(CNc2nccc(-c3cccnc3)n2)cc1]

N-(2-Aminophenyl)-4-[[(4-pyridin-3-ylpyrimidin-2-yl)amino]methyl]benzamide

Further examples of such HDAC inhibitors are included in Bertrand European Journal of Medicinal Chemistry 45, (2010) 2095-2116, particularly the compounds of table 3 therein as indicated below.

Hydroxamic acids

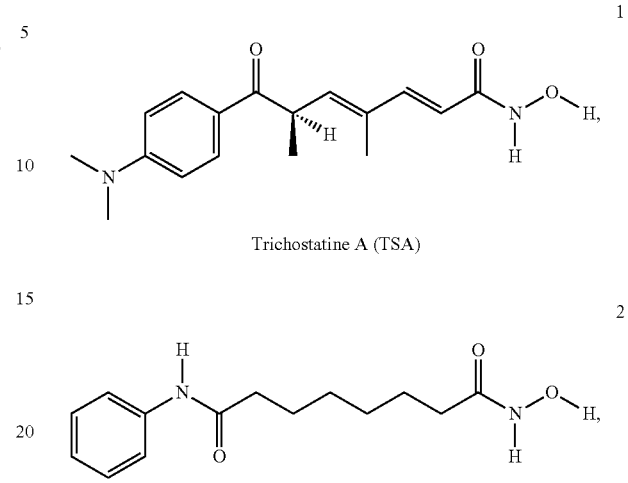

Trichostatine A (TSA)

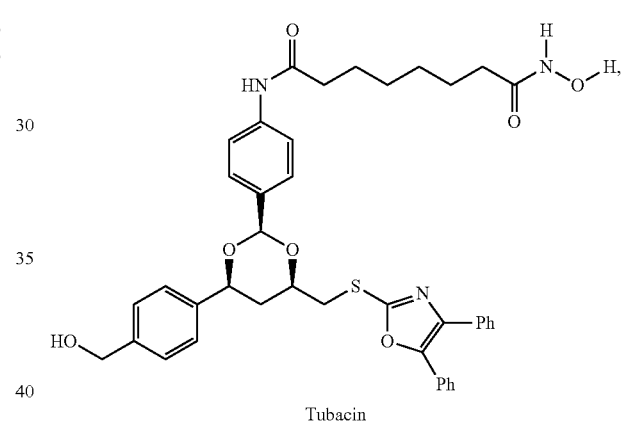

SAHA

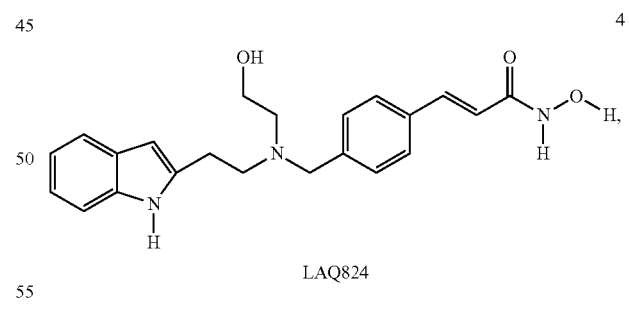

Tubacin

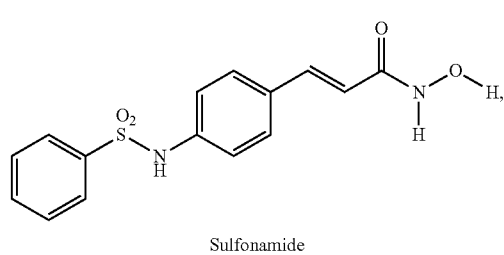

LAQ824

Sulfonamide

-continued

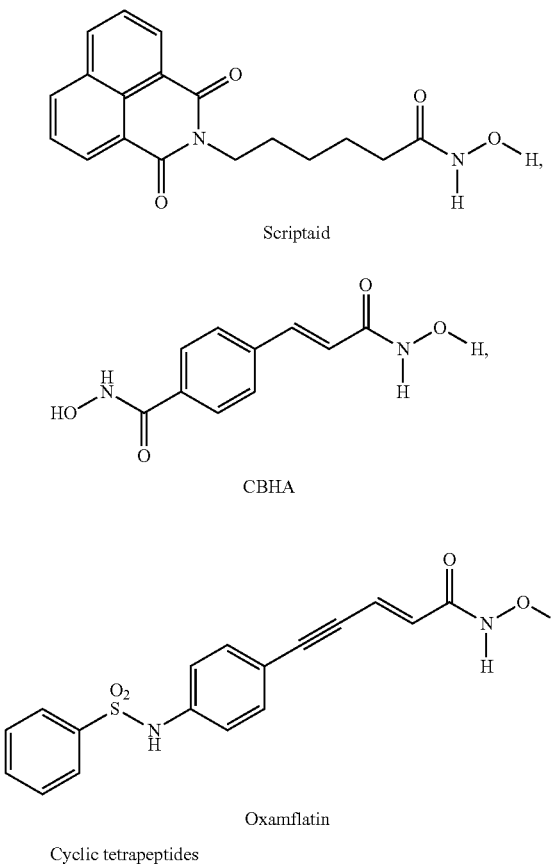

Scriptaid

CBHA

Oxamflatin

Cyclic tetrapeptides

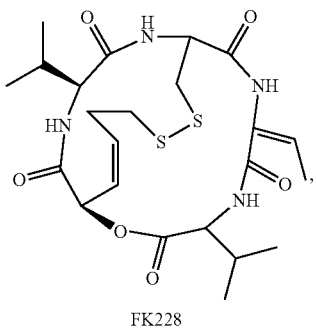

FK228

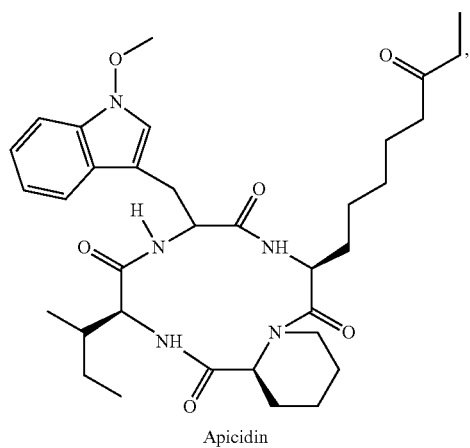

Apicidin

-continued

Short chain carboxylic acids

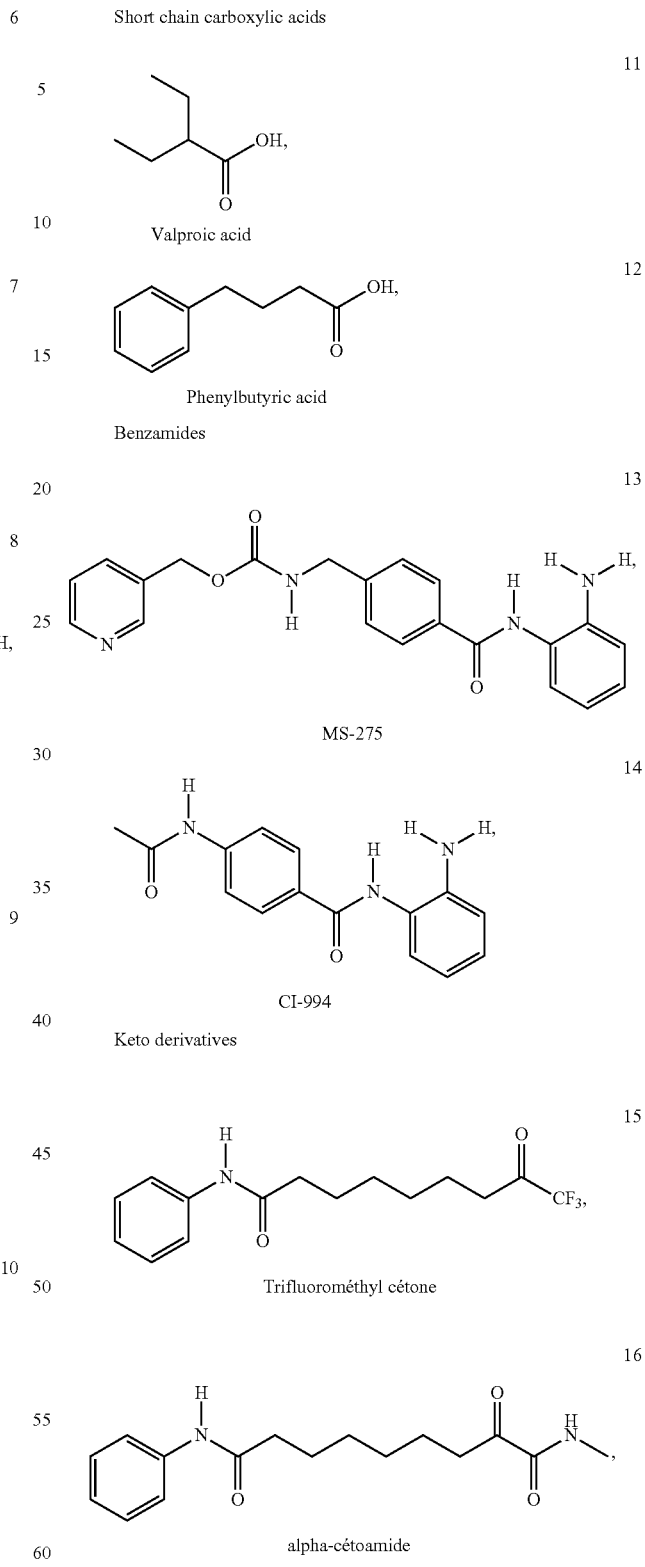

Valproic acid

Phenylbutyric acid

Benzamides

MS-275

CI-994

Keto derivatives

Trifluorométhyl cétone alpha-cétoamide

Proteasome inhibitors are drugs that block the action of proteasomes, cellular complexes that break down proteins, like the p53 protein. Several proteasome inhibitors are marketed or are being studied in the treatment of cancer. Suitable proteasome inhibitors for use herein include:

1. Bortezomib (Velcade®), including pharmaceutically acceptable salts thereof. Adams J, Kauffman M (2004), *Cancer Invest* 22 (2): 304-11.
Bortezomib has the following chemical structure and name.

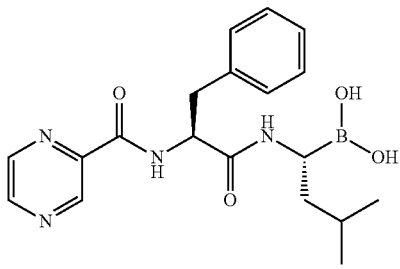 [SMILES: CC(C)C[C@H](NC(=O)[C@H](Cc1ccccc1)NC(=O)c1cnccn1)B(O)O]

[(1R)-3-methyl-1-({(2S)-3-phenyl-2-[(pyrazin-2-ylcarbonyl)amino]propanoyl}amino)butyl]boronic acid 2. Disulfuram, including pharmaceutically acceptable salts thereof.
Bouma et al. (1998). *J. Antimicrob. Chemother.* 42 (6): 817-20.
Disulfuram has the following chemical structure and name.

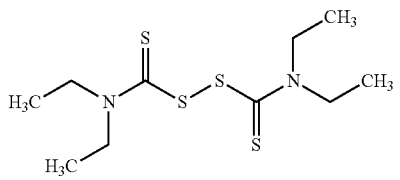 [SMILES: CCN(CC)C(=S)SSC(=S)N(CC)CC]

1,1',1'',1'''-[disulfanediylbis(carbonothioylnitrilo)]tetraethane

3. Epigallocatechin gallate (EGCG), including pharmaceutically acceptable salts thereof. Williamson et al., (December 2006), *The Journal of Allergy and Clinical Immunology* 118 (6): 1369-74.
Epigallocatechin gallate has the following chemical structure and name.

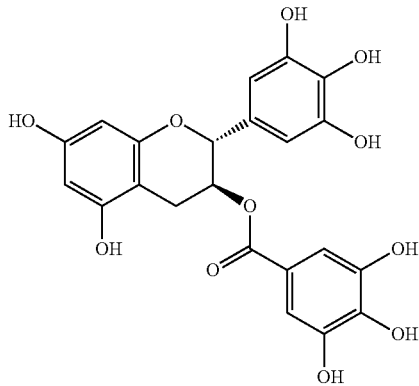 [SMILES: O=C(O[C@H]1Cc2c(O)cc(O)cc2O[C@@H]1c1cc(O)c(O)c(O)c1)c1cc(O)c(O)c(O)c1]

[(2R,3R)-5,7-dihydroxy-2-(3,4,5-trihydroxyphenyl)chroman-3-yl]3,4,5-trihydroxybenzoate 4. Salinosporamide A, including pharmaceutically acceptable salts thereof. Feling et at., (2003), *Angew. Chem. Int. Ed. Engl.* 42 (3): 355-7.
Salinosporamide A has the following chemical structure and name.

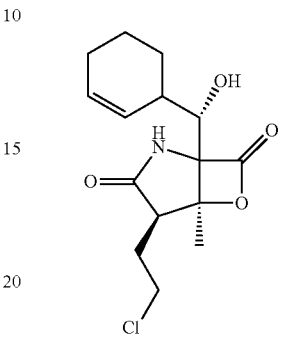

(4R,5S)-4-(2-chloroethyl)-1-((1S)-cyclohex-2-enyl(hydroxy)methyl)-5-methyl-6-oxa-2-azabicyclo3.2.0heptane-3,7-dione Inhibitors of cancer metabolism—Many tumor cells show a markedly different metabolism from that of normal tissues. For example, the rate of glycolysis, the metabolic process that converts glucose to pyruvate, is increased, and the pyruvate generated is reduced to lactate, rather than being further oxidized in the mitochondria via the tricarboxylic acid (TCA) cycle. This effect is often seen even under aerobic conditions and is known as the Warburg Effect.

Lactate dehydrogenase A (LDH-A), an isoform of lactate dehydrogenase expressed in muscle cells, plays a pivotal role in tumor cell metabolism by performing the reduction of pyruvate to lactate, which can then be exported out of the cell. The enzyme has been shown to be upregulated in many tumor types. The alteration of glucose metabolism described in the Warburg effect is critical for growth and proliferation of cancer cells and knocking down LDH-A using RNA-i has been shown to lead to a reduction in cell proliferation and tumor growth in xenograft models.
D. A. Tennant et. al., *Nature Reviews*, 2010, 267.
P. Leder, et. al., *Cancer Cell*, 2006, 9, 425.

Inhibitors of cancer metabolism, including inhibitors of LDH-A, are suitable for use in combination with the compounds of this invention.

By the term "dry blend" and derivatives thereof, as used herein refers to formulated particles that comprise Compound A and/or diluents and/or binders and/or lubricants and/or disintegrants such that the particles are suitable for utilization in preparing solid oral pharmaceutical dosage forms, suitably tablets, suitably capsules and are produced by dry blending or dry granulation. It is possible to administer the dry blend directly to a subject in need thereof as a medicament. However, it is anticipated that the dry blend are most appropriately utilized in the preparation of solid oral pharmaceutical dosage forms, suitably tablets, suitably capsules, as indicated above.

By the term "solid oral pharmaceutical dosage form" and "solid dosage form" and derivatives thereof, as used herein, unless otherwise defined, refers to a final pharmaceutical preparation that comprises Compound A, such as: tablets, capsules, pellets, lozenges, sachets and powders (including coated versions of any of such preparations), suitably tablets, suitably capsules, that are suitable for in vivo administration.

When indicating that an excipient for use herein is substantially free of water, it is contemplated that the excipient could contain minor amounts of water, for example: about 5% by weight or less, suitably about 2.5% by weight of less, suitably about 1% by weight of less. In this aspect of the invention, it is believed that very minor amounts of water can be in the excipient component without adversely affecting the performance of the solid dosage from, suitably the tablet, suitably the capsule.

Suitably, the solid oral pharmaceutical dosage forms of the present invention comprise Compound A, a diluent (also known as filler or bulking agent), and suitably also a binder and/or a lubricant and/or a disintegrant. Those skilled in the art will recognize that a given material may provide one or more functions in the tablet formulation, although the material is usually included for a primary function. The percentages of diluent, binder, lubricant and disintegrant provided herein and in the claims are by weight of the tablet.

Diluents provide bulk, for example, in order to make the tablet a practical size for processing. Diluents may also aid processing, for example, by providing improved physical properties such as flow, compressibility, and tablet hardness. Because of the relatively high percentage of diluent and the amount of direct contact between the diluent and the active compound in the typical pharmaceutical formulation, the interaction of the diluent with the active compound is of particular concern to the formulator. Examples of diluents suitable for use in the present invention include either the following or an anhydrous version thereof: water-soluble fillers and water-insoluble fillers, such as calcium phosphate (e.g., di and tri basic, hydrated or anhydrous), calcium sulfate, calcium carbonate, magnesium carbonate, kaolin, lactose that is substantially free of water, suitably spray dried or anhydrous lactose (collectively lactose as used herein), cellulose (e.g., microcrystalline cellulose, powdered cellulose), pregelatinized starch, starch, lactitol, mannitol, sorbitol, maltodextrin, powdered sugar, compressible sugar, sucrose, dextrose, and inositol. Diluents that are substantially free of water are suitable for tablets of the current invention. In one embodiment of the present invention, the diluent is composed of one or both of Mannitol and microcrystalline cellulose.

The solid oral pharmaceutical dosage forms of the present invention typically comprise from about 25% to about 89%, of one or more diluents.

One aspect of the present invention comprises solid oral pharmaceutical dosage forms wherein the solid dosage forms are formulated using a diluent or diluents that are substantially free of water.

One aspect of the present invention comprises pharmaceutical tablets, wherein the tablets are formulated using a diluent or diluents that are substantially free of water.

One aspect of the present invention comprises pharmaceutical capsules, wherein the capsules are formulated using a diluent or diluents that are substantially free of water.

Binders impart cohesive properties to the powdered material. Examples of binders suitable for use in the present invention include either the following or an anhydrous version thereof: hydroxypropyl methyl cellulose (HPMC), hydroxypropyl cellulose (HPC), hydroxyethyl cellulose (HEC) and ethyl cellulose (EC)], polyvinylpyrrolidone. Binders that are substantially free of water are suitable for tablets of the current invention. In one embodiment of the present invention, the binder is hydroxypropyl methyl cellulose (HPMC) or Hypromellose.

The solid oral pharmaceutical dosage forms of the present invention typically comprise up to about 2-8% binder such as about 2%, about 3%, about 4%, about 5%, about 6% about 7%, and about 8% w/w. The formulations suitably comprise up to about 5% binder.

One aspect of the present invention comprises solid oral pharmaceutical dosage forms wherein the solid dosage forms are formulated using a binder or binders that are substantially free of water.

One aspect of the present invention comprises pharmaceutical tablets, wherein the tablets are formulated using a binder or binders that are substantially free of water.

One aspect of the present invention comprises pharmaceutical capsules, wherein the capsules are formulated using a binder or binders that are substantially free of water.

Lubricants are generally used to enhance processing, for example, to prevent adhesion of the formulation material to manufacturing equipment, reduce interparticle friction, improve rate of flow of the formulation, and/or assist ejection of the formulations from the manufacturing equipment. Examples of lubricants suitable for use in the present invention include either the following or an anhydrous version thereof: talc, stearates (e.g., magnesium stearate, calcium stearate, zinc stearate, palmitostearate), stearic acid, hydrogenated vegetable oils, glyceryl behanate, polyethylene glycol, ethylene oxide polymers (e.g., CARBOWAXes), liquid paraffin, sodium lauryl sulfate, magnesium lauryl sulfate, sodium oleate, sodium stearyl fumarate, DL-leucine, and silica derivatives (e.g., colloidal silicon dioxide, colloidal silica, pyrogenic silica, and sodium silicoaluminate). Lubricants that are substantially free of water are suitable for tablets of the current invention. In one embodiment of the present invention, the lubricant is magnesium stearate.

The solid oral pharmaceutical dosage forms of the present invention typically comprise up to about 2% lubricant. The formulations suitably comprise up to about 1%, suitably up to about 0.75% lubricant.

One aspect of the present invention comprises solid oral pharmaceutical dosage forms wherein the solid dosage forms are formulated using a lubricant or lubricants that are substantially free of water.

One aspect of the present invention comprises pharmaceutical tablets, wherein the tablets are formulated using a lubricant or lubricants that are substantially free of water.

One aspect of the present invention comprises pharmaceutical capsules, wherein the capsules are formulated using a lubricant or lubricants that are substantially free of water.

Disintegrants are employed to facilitate breakup or disintegration of the formulation after administration. Examples of disintegrants suitable for use in the present invention include either the following or an anhydrous version thereof: starches, celluloses, gums, crosslinked polymers, and effervescent agents, such as corn starch, potato starch, pregelatinized starch, modified corn starch, croscarmellose sodium, crospovidone, sodium starch glycolate, Veegum HV, methyl cellulose, microcrystalline cellulose, cellulose, colloidal silicon dioxide, modified cellulose gum (e.g., Ac-Di-Sol R), agar, bentonite, montmorillonite clay, natural sponge, cation exchange resins, ion exchange resins (e.g., polyacrin potassium), alginic acid and alginates, guar gum, citrus pulp, carboxymethylcellulose and salts thereof such as sodium lauryl sulfate, magnesium aluminum silicate, hydrous aluminum silicate, sodium bicarbonate in admixture with an acidulant such as tartaric acid or citric acid. Disintegrants that are substantially free of water are suitable for tablets of the current invention. In one embodiment of the present invention, the disintegrant is composed of one or more of: croscarmellose sodium, sodium lauryl sulfate and colloidal silicon dioxide.

The solid oral pharmaceutical dosage forms of the present invention typically comprise an amount from 2% to about 5% disintegrant, suitably about 2%, about 3%, about 4%, and about 5% w/w. The formulations suitably comprise about 3% disintegrant.

One aspect of the present invention comprises solid oral pharmaceutical dosage forms wherein the solid dosage forms are formulated using a disintegrant or disintegrants that are substantially free of water.

One aspect of the present invention comprises pharmaceutical tablets, wherein the tablets are formulated using a disintegrant or disintegrants that are substantially free of water.

One aspect of the present invention comprises pharmaceutical capsules, wherein the capsules are formulated using a disintegrant or disintegrants that are substantially free of water.

When administered in vivo, each pharmaceutical compound acts uniquely in regards to therapeutic drug levels. Further, pharmaceutically active compounds are often associated with undesirable side effects such as; toxicity (e.g. genotoxicity, teratogenicity) and undesirable physical or psychological manifestations. In addition to balancing the drug's chemical properties with those of the excipients, the drug must be administered at a specific amount that is sufficient to provide the desired therapeutic drug level but less than the amount that presents an unacceptable side effect profile, or within a therapeutic window for that particular drug. One embodiment of this invention is directed to administering Compound A in an amount sufficient to provide the desired therapeutic effect and an acceptable side effect profile.

Dosing Strength

Numerous studies using N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide were conducted in animal models in an attempt to establish a dose selection range for human studies. The animal models included the following.

Pharmacokinetics and Metabolism in Animals

The pharmacokinetics, absorption, distribution, metabolism and elimination of N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide and solvates thereof, including the dimethyl sulfoxide solvate (collectively referred to as "Compound" when used in connection with animal models or human clinical trials), were investigated in a series of in vitro investigations and with in vivo oral (gavage) and IV studies in the Balb/c mouse, Sprague Dawley rat (unless otherwise stated), beagle dog and cynomolgus monkey using unlabeled and [14C]-labeled Compound. A list of these studies is included, along with subsequently obtained human clinical results, in Table 1 below. For in vivo studies, various formulations were used. For oral dosing, solutions or suspensions were administered. Further, some pharmacokinetic and toxicity studies utilized micronized Compound, including the 13 week toxicity studies in rats and dogs.

TABLE 1

List of Pharmacokinetic and Product Metabolism Studies with "Compound"

| Type of Study | Route | Dose (mg/kg) [mg/m$^2$] | Form | Species | No./Group |
|---|---|---|---|---|---|
| Single Dose | | | | | |
| | IV or Oral | 0.3 to 3 | A/B/H$^{SOL}$ | Mouse | 3 F |
| | IV or Oral | 0.3 to 10 | A/B/H$^{SOL}$ | Rat | 3 M |
| | IV or Oral | 0.3 | A/H$^{SOL}$ | Dog | 3 M |
| | IV or Oral | 0.3 | B | Monkey | 3 M |
| Dose escalation | Oral | 3, 10, 30, 100 [24, 80, 240, 800] | H$^{SOL}$ | Rat | 3 M |
| Dose escalation | Oral | 0.013 to 3 [0.25 to 60] | B | Dog | 1 M/1 F |
| Repeat Dose Toxicokinetics | | | | | |
| up to 13 weeks | Oral | [0.125 up to 24] | B | Rat | Up to 18 M/F |
| up to 13 weeks | Oral | [0.1510] | B | Dog | up to 6 M/6 F |
| Distribution | | | | | |
| Plasma protein binding | In vitro | 5 μM | A | nonclin species | NA |
| Blood cell association | | 0.5, 5 μg/mL | | Human | |
| Pgp substrate and passive permeability | In vitro | up to 5 μM | B/[$^{14}$C]B | Human | NA |
| Inhibition of Pgp/OATP1B1/1B3 | In vitro | up to 50 μM | B | Human | NA |
| BCRP substrate; passive permeability and inhibition | In vitro | up to 100 μM | [$^{14}$C]B/B | Human | NA |
| Permeability in MDCKII-MDR1 | In vitro | 0.115 to 11.5 μM | B | Human | NA |
| QWBA | Oral | 1 [8] | [$^{14}$C]B | Rat | 7 M |
| Blood, plasma and liver concentrations | Oral | 1 [8] | [$^{14}$C]B | Rat | 15 M/15 F |
| Blood and plasma concentrations | Oral | 0.5 [10] | [$^{14}$C]B | Dog | 3 M/3 F |
| Metabolism | | | | | |
| Human blood stability | In vitro | 5 μg/mL | B | Human | NA |
| Intrinsic clearance | In vitro | up to 10 μM | A or B | nonclin species, Human | NA |
| Metabolic stability and profiling | | | | | |
| Oxidative metabolism | In vitro | 5 μM | [$^{14}$C]B | Human | NA |
| Oxidative bioactivation | In vitro | 10 μM | [$^{14}$C]B | Human | NA |

TABLE 1-continued

List of Pharmacokinetic and Product Metabolism Studies with "Compound"

| Type of Study | Route | Dose (mg/kg) [mg/m²] | Form | Species | No./Group |
|---|---|---|---|---|---|
| Hepatic metabolism | In vitro | 12.5 μM | [¹⁴C]B | nonclin species, Human | NA |
| Hepatic metabolism (IPRL) | In situ | 30 | [¹⁴C]B | Rat | 5 |
| CYP inhibition (3 studies conducted) | In vitro | 0.01 to 50 μM | A or B | Human | NA |
| PXR activation | In vitro | 0.0002 to 10 μM | B | Rat and Human | NA |
| CYP induction | In vitro | 0.01 to 10 μM | B | Human | 3 |
| CYP induction | Oral | 0.1, 0.3, 1 [0.8, 2.4, 8] | B | Rat | 4 M |
| Excretion | | | | | |
| Elimination | Oral | 1 [8] | [¹⁴C]B | Rat | 3 M/3 F 3M (BDC) |
| Elimination | Oral | 0.5 [10] | [¹⁴C]B | Dog | 3 M/3 F |

A = Compound (parent form);
B = Compound (dimethylsulfoxide solvate);
H = Compound (acetic acid solvate);
[¹⁴C] = [¹⁴C]-labeled Compound (DMSO solvate);
BCRP = Breast cancer resistance protein;
BDC = Bile duct cannulated;
CYP = Cytochrome P450;
HEK = Human embryonic kidney;
IV = Intravenous;
M = Male;
F = Female;
NA = Not applicable;
MDCKII-MDR1 = Madin-Darby canine kidney type II - multidrug resistance 1;
OATP = Organic anion transporting polypeptide;
Pgp = P-glycoprotein;
PXR = Pregnane X receptor;
QWBA = Quantitative whole body autoradiography;
SOL = Solution formulation.
NOTE:
Oral doses were administered by gavage (using suspension formulations unless otherwise noted).

Repeat Dose Pharmacokinetics and Toxicology

Comparative systemic exposure (AUC0-t and Cmax) for 13 week studies in rats and dogs are presented in Table 2. Dose range studies in rats at doses up to 1 mg/kg/day for 14 days and in dogs at doses up to 0.5 mg/kg/day (or 10 mg/m2/day) for 10 days were conducted prior to the studies.

TABLE 2

Comparative Assessment of Mean Systemic Exposure Following Oral Administration of Compound to Rats, Dogs and Humans

| Species (Duration) | Dose (mg/m²/day) | Sex | $C_{max}$ (ng/mL) | | AUC (ng·h/mL) | |
|---|---|---|---|---|---|---|
| | | | End of Study | Animal to Human Ratio[a] | End of Study | Animal to Human Ratio[a] |
| Rat (3 weeks) | 0.125 | M | 1.78 | 0.08 | 35.0 | 0.10 |
| | | F | 3.33 | 0.14 | 60.2 | 0.17 |
| | 0.25 | M | 3.50 | 0.15 | 64.2 | 0.18 |
| | | F | 6.28 | 0.27 | 126 | 0.35 |
| | 0.5 (MTD) | M | 7.78 | 0.33 | 129 | 0.36 |
| | | F | 13.0 | 0.56 | 211 | 0.59 |
| | 1 (MTD) | M | 13.3 | 0.57 | 218 | 0.61 |
| | | F | 29.4 | 1.26 | 460 | 1.28 |
| Rat (13 weeks) | 0.125 | F | 5.30 | 0.23 | 102 | 0.28 |
| | 0.25 (MTD) | M | 5.34 | 0.23 | 95.4 | 0.27 |
| | | F | 8.03 | 0.34 | 158 | 0.44 |
| | 0.5 | M | 15.4[b] | 0.66 | 277[b] | 0.77 |
| | | F | NC | NC | NC | NC |
| | 1.0 | M | NC | NC | NC | NC |
| Dog (3 weeks) | 0.3 | F | 7.19 | 0.31 | 120 | 0.33 |
| | 0.4[c] | F | 11.6 | 0.50 | 211 | 0.59 |
| | 0.5 (MTD)[c] | F | 12.3 | 0.53 | 205 | 0.57 |
| | | M | 9.37 | 0.40 | 159 | 0.44 |
| | 0.75[c] | M | 19.0[d] | 0.82 | 282[d] | 0.78 |
| | 1.5[c,e] | M | NC | NC | NC | NC |

TABLE 2-continued

Comparative Assessment of Mean Systemic Exposure Following
Oral Administration of Compound to Rats, Dogs and Humans

| Species (Duration) | Dose (mg/m²/day) | Sex | $C_{max}$ (ng/mL) End of Study | $C_{max}$ Animal to Human Ratio[a] | AUC (ng·h/mL) End of Study | AUC Animal to Human Ratio[a] |
|---|---|---|---|---|---|---|
| Dog (13 weeks) | 0.15 | M | 2.32 | 0.10 | 45.6 | 0.13 |
|  |  | F | 2.71 | 0.12 | 51.8 | 0.14 |
|  | 0.3 | M | 5.15 | 0.22 | 95.5 | 0.27 |
|  |  | F | 7.24 | 0.31 | 107 | 0.30 |
|  | 0.45 (NOAEL)[f] | M | 8.42 | 0.36 | 128 | 0.36 |
|  |  | F | 9.78 | 0.42 | 150 | 0.42 |
| Human | 2 mg | M&F | 23.3 | NA | 360 | NA |

NA = Not applicable; NC = Not calculated.
Note:
Data are the means (n = 3) except as noted. Bolded values are maximum tolerated dose (MTD) or No Observed Adverse Effect Level (NOAEL) as indicated.
[a]Ratios given with respect to mean human exposures on Day 15 of daily dosing at a dose of 2 mg.
[a]Data obtained from 2 rats.
[b]Data obtained from 5 dogs.
[c]Data obtained from 4 dogs.
[d]For dogs given 1.5 mg/m²/day, the last day of dosing was Day 7.
[e]Dogs received 0.6 mg/m²/day for first 11 to 12 days, an approximate 7 day drug holiday and then 0.45 mg/m²/day for the remainder of the study.

In vivo toxicology studies were conducted in Sprague Dawley rats and beagle dogs by oral gavage (Table 3). Studies were conducted using the DMSO solvate of Compound formulated as a suspension in 1.5% hydroxypropylmethylcellulose, 5% mannitol, and 0.2% sodium lauryl sulfate. For all toxicology studies, doses are expressed based on body surface area (mg/m2). In general, to convert mg/m2 doses to mg/kg, divide the doses by 8 for rats and 20 for dogs.

TABLE 3

Toxicology Studies Conducted with Compound

| Type of Study | Route | Dose [mg/m²] | Form | Species | No./Group |
|---|---|---|---|---|---|
| Single Dose |  |  |  |  |  |
| Dose escalation | Oral | 24, 80, 240, 800 | H | Rat | 3 M |
| Dose escalation | Oral | 3, 10, 60 | B | Dog | 1 M/F |
| Repeat Dose |  |  |  |  |  |
| 3 days | Oral | 2.4, 24, 240 | H | Rat | 5 M |
| 14 days (4 studies conducted) | Oral | 0.8 to 24 | H | Rat | up to 4 M/4 F |
| 3 weeks | Oral | 0.125, 0.25, 0.5, 1 | B | Rat | 10 to 16 M/F |
| 13 weeks[a] | Oral | M: 0.25, 0.5, 1.0 F: 0.125, 0.25, 0.5 | B | Rat | 12 to 18 M/F |
| 10 days | Oral | 2.5, 5, 10 | B | Dog | 1 M/F |
| 3 weeks | Oral | M: 0.5, 0.75, 1.5 F: 0.3, 0.4, 0.5 | B | Dog | 3 to 5 M/F |
| 13 weeks[a] | Oral | 0.15, 0.3, 0.6/0.45 | B | Dog | 4 to 6 M/F |
| Genotoxicity |  |  |  |  |  |
| Ames | In vitro | 1.5 to 2500 μg/plate | B | NA | NA |
| Mouse lymphoma | In vitro | 5 to 150 μg/mL | B | NA | NA |
| Micronucleus | Oral | 7.3, 14.4 | B | Rat | 7 M |

B = Compound (dimethylsulfoxide solvate);
H = Compound (acetic acid solvate);
M = Male;
F = Female;
NA = Not applicable.
f. 13 week repeat dose toxicity study followed by a 4 week recovery period.

In view of the results observed in animal models, dose range studies for single dose and multiple dose human clinical trials were conducted.

Pharmacokinetics, Product Metabolism, and Pharmacodynamics in Humans

Preliminary PK data was obtained in subjects with solid tumors following single- and repeat-dose oral administration of Compound tablets. The dose-escalation part of the first-time-in-human study (FTIH), involved administration of Compound in one of 3 main dosing regimens:

QD dosing with the designated dose for 21 days, followed by 7 days without drug;

Administration of a loading dose (LD) on both Day 1 and Day 2, or on Day 1 only, followed by continuous QD dosing with the designated dose; or Administration of continuous QD dosing without a loading dose.

Single-Dose Pharmacokinetics

Single dose (Day 1) pharmacokinetics of Compound were evaluated after oral administration of Compound tablets under fasting conditions in the ongoing FTIH study and preliminary results are depicted in Table 4. Plasma concentrations for Compound were not measurable for all subjects over the 24-hour time period, especially for subjects administered low doses ranging from 0.125-0.50 mg. In general, AUC (0-24) and Cmax values were dose proportional up to 6 mg, lower than dose proportional following 8 mg and greater than dose proportional following the 10 mg dose. Most subjects had samples taken up to 24 hrs following single dose and half-life and AUC(O-inf) could not be calculated. Median Tmax ranged from 1.0 to 3.0 hours. Mean variability (CV %) in exposure ranged from 13 to 68% for Cmax and 12 to 56% for AUC (0-24) across all dosing regimens.

TABLE 4

Preliminary Pharmacokinetic Parameters Following Single Dose Administration of Compound (Day 1)

| Dose (mg) | N | AUC (0-24) (ng * hr/mL) | Cmax (ng/mL) | Tmax (hr) | C24 (ng/mL) |
|---|---|---|---|---|---|
| 0.125 | 2ª | NA | 0.62, 0 | 0.50, NA | 0, 0 |
| 0.25 | 1ª | NA | 0.34 | 1.03 | 0 |
| 0.5 | 2 | 2.13, 9.69 | 0.85, 1.21 | 1.5, 1.5 | 0, 0.31 |

TABLE 4-continued

Preliminary Pharmacokinetic Parameters Following Single Dose Administration of Compound (Day 1)

| Dose (mg) | N | AUC (0-24) (ng * hr/mL) | Cmax (ng/mL) | Tmax (hr) | C24 (ng/mL) |
|---|---|---|---|---|---|
| 1.0 | 2 | 13.5, 12.2 | 1.71, 1.96 | 1.5, 1.5 | 0.38, 0.27 |
| 2.0 | 3 | 56.2 (33%) (44.2-77.4) | 6.83 (26%) (5.40-8.81) | 1.5 (1.5-2.0) | 1.49 (27%) (1.15-1.93) |
| 2.5 | 9 | 71.1 (25%) (47.3-95.9) | 9.68 (32%) (6.70-16.2) | 1.5 (1.0-2.0) | 1.81 (34%) (1.25-3.10) |
| 3.0 | 12 | 81.4 (54%) (27.6-188) | 11.5 (62%) (2.82-22.9) | 1.25 (0.5-3.0) | 3.35 (101%) (0.75-13.4) |
| 4.0 | 3 | 223 (24%) (167-275) | 27.1 (35%) (16.3-34.2) | 1.0 (1.0-1.0) | 8.77 (60%) (5.53-14.9) |
| 6.0ᵇ | 10 | 197 (46%) (96.7-320) | 23.2 (50%) (6.91-37.2) | 1.5 (1.05-8.08) | 6.58 (41%) (3.4-11.1) |
| 8.0ᵇ | 7 | 161 (56%) (62.9-308) | 14.9 (68%) (4.28-32.0) | 3.0 (1.0-24.0) | 5.81 (50%) (2.98-12.1) |
| 10.0ᵇ | 4 | 884 (12%) (773-979) | 78.7 (13%) (65.1-87.8) | 1.5 (1.0-2.0) | 25.5 (15%) (21.0-29.0) |

Abbreviations:
BQL = Below quantitation limit of the assay;
NA = Not available
Note:
Pharmacokinetic parameters listed for individuals if patient number <=2; listed as mean (CV%) and range if patient number >2; Tmax reported as median (range); $T_{1/2}$ not displayed as a terminal phase could not be identified
g. Subjects in the low dose cohorts had limited samples (≤3 quantifiable samples) and AUC is not reported; One subject had BQL for all samples
h. Administered as loading dose on Day 1

Multiple-Dose Pharmacokinetics

Repeat dose (Day 15) pharmacokinetics of Compound were assessed after oral administration of Compound tablets under fasting conditions in the FTIH study and preliminary results are depicted in Table 5. Compound accumulated with repeat daily dosing with a mean accumulation ratio at the recommended dose of 2 mg QD of 6.6. Mean AUC (0-tau) and Cmax values on Day 15 generally increased in a dose-proportional manner (i.e., 2-fold increase in dose resulted in a 2-fold increase in exposure). Due to the long elimination phase, an effective half-life (T½, eff) of approximately 5 days was calculated based on the accumulation ratio. Between-subject variability (CV %) in exposure ranged from 27 to 50% for Cmax and 20 to 41% for AUC (0-24) across all dosing regimens.

TABLE 5

Preliminary Pharmacokinetic Parameters Following Repeat Dose Administration of Compound (Day 15)

| Dose (mg) | N | AUC(0-24) (ng · h/mL) | Cmax (ng/mL) | Tmax (h) | C24 (ng/mL) | AR | T½, eff (days) |
|---|---|---|---|---|---|---|---|
| 0.125 | 2 | 17.8, 14.6 | 1.21, 1.58 | 1.0, 1.5 | 0.66, 0.58 | NA | NA |
| 0.25 | 1 | 31.1 | 2.08 | 1.5 | 1.16 | NA | NA |
| 0.50 | 2 | 60.1, 98.9 | 3.91, 5.38 | 2.1, 1.0 | 2.21, 4.29 | 28.3, 10.2 | 19.2, 6.7 |
| 1 | 2 | 243, 95.2 | 15.8, 7.96 | 0.75, 1.5 | 8.44, 19.1 | 18.1, 7.8 | 12.2, 5.1 |
| 2ª | 12 | 376 (20%) (255-500) | 23.0 (27%) (14.1-32.9) | 1.75 (1.0-3.0) | 12.3 (19%) (8.26-16.9) | 6.57 (36%) (4.0-11.5) | 4.20 (39%) (2.43, 7.61) |
| 2.5ª | 15 | 448 (41%) (215-865) | 26.7 (50%) (12.4-63.2) | 2.0 (1.0-24) | 17.0 (53%) (6.86-40.5) | 8.14 (42%) (3.23-14.1) | 5.29 (45%) (1.87-9.40) |
| 3ª | 14 | 575 (36%) (259-968) | 35.8 (39%) (15.6-60.9) | 2.10 (0.5-10.0) | 19.5 (42%) (7.77-35.5) | 7.17 (64%) (1.50-17.8) | 4.60 (72%) (0.63-12.0) |
| 4 | 2ᵇ | 549, 946 | 43.8, 62.8 | 1.5, 1.0 | 42.8, 8.01 | 2.42, 3.45 | 1.30, 2.02 |

Abbreviations: AR = Accumulation Ratio; NA = Not applicable; T½, eff = Effective Half-Life
Note:
Pharmacokinetic parameters listed for individuals if patient number <=2; listed as mean (CV %), and (min-max) if patient number >2; Tmax is reported as median (range).
i. Contains subjects at both loading and continuous dosing regimens.
j. Subject 1210 omitted from analysis due to drug being withheld.

Additional blood samples were taken pre-dose on Day 15 of Cycle 1 and Day 1 of further cycles in Part 2 and Part 3 to assess steady state trough levels of Compound. Mean trough concentrations after repeat dosing up to 10 cycles ranged from 10.0 to 18.9 ng/mL following 2.0 mg daily and from 7.8 to 17.3 ng/mL following 2.5 mg. Mean (CV %) trough concentrations on Day 15 after repeat dosing of 2.5 mg of Compound were 16.8 ng/mL (54%) and ranged from 0.68 to 49.0 ng/mL.

After reviewing all available data, a dose of 2 mg administered once daily was selected based on tolerability, exposure-response relationship with pharmacodynamic markers in tumor biopsies, and clinical activity. A 0.5 mg dose was also selected to accommodate lower strength dosing, for example when used in combination with another anti-neoplastic compound or when dose reduction is required due to toxicity.

Photostability of Drug Product

During the formulation development of Compound A, it was found that the level of two degradation products observed at RRT=0.81 and RRT=0.87 (by HPLC analysis) exceeded the ICH limit for unqualified impurities of 0.5% when exposed directly to ICH Q1B light conditions.

Coating Effect on Light Exposure

Uncoated tablets, 0.5, 1 and 2 mg were exposed to ICH Photostability conditions and tested to provide baseline impurity information for comparison. Data in Table 6 shows that the impurities at RRT=0.81 and RRT=0.87 are greater than 0.5% for tablet cores prior to coating.

The composition of coatings studied is given in Table 7. Among the five coating formulations investigated, Opadry® white provided the least amount of protection for 1 mg strength, as the observed impurity levels appear to be similar to the uncoated tablets. Two different formulations of Opadry® pink and Opadry® yellow were tested and all provided adequate light protection.

Data from 1 mg showed that both formulations of Opadry® pink and yellow provided adequate light protection. This protection does not change when the level of colorant is decreased from 4 to 2% w/w. With the protection of Opadry® pink or yellow, all coated tablets demonstrated good photostability even under direct light exposure (tablets in Petri dish).

TABLE 6

Light Exposure of Core (Uncoated) Tablets in Petri Dish

| Strength (mg) | Impurity (% area) RRT = 0.81 | Impurity (% area) RRT = 0.87 | Impurity (% area) RRT = 0.89 |
|---|---|---|---|
| 0.5 | 0.73 | 0.90 | 0.07 |
| 1 | 0.50 | 0.61 | <0.05 |
| 2 | 0.80 | 0.58 | 0.07 |

TABLE 7

Composition of Coatings

| Component | Opadry Formulation (% w/w) | | | | |
|---|---|---|---|---|---|
| | White (OY-S-28876) | Pink 1 (YS-1-14762-A) | Pink 2 (03B140009) | Yellow 1 (YS-1-12525-A) | Yellow 2 (03B120006) |
| Hypromellose 3cP | — | 29.50 | — | 32.58 | — |
| Hypromellose 6cP | 63.00 | 29.50 | 63.00 | 32.58 | 63.00 |
| Titanium dioxide | 30.00 | 31.04 | 29.00 | 21.79 | 28.00 |
| Macrogol/PEG400 | 7.00 | 8.00 | 7.00 | 8.00 | 7.00 |
| Polysorbate 80 | — | 1.00 | — | 1.00 | — |
| Iron Oxide Red | — | 0.96 | 1.00 | — | — |
| Iron Oxide Yellow | — | — | — | 4.05 | 2.00 |

TABLE 8

Light Exposure of Coated Tablet in Petri Dish

| Strength (mg) | Coating | Impurity (% area) | | |
|---|---|---|---|---|
| | | RRT = 0.81 | RRT = 0.87 | RRT = 0.89 |
| 0.5 | White | 2.0 | 0.40 | ND |
| | Yellow-2 | 0.94 | 0.08 | ND |
| | Pink-1 | 0.16 | 0.19 | ND |
| | Pink-2 | 0.14 | 0.16 | <0.05 |
| 1 | White | 0.58 | 0.44 | <0.05 |
| | Yellow-1 | 0.10 | 0.13 | ND |
| | Yellow-2 | 0.10 | 0.13 | ND |
| | Pink-2 | 0.07 | 0.06 | ND |
| 2 | Pink-1 | 0.09 | <0.05 | ND |

ND = Not detected.

Impurity Characterization

Although three impurities were observed during photostability studies, impurities at RRT=0.81 and RRT=0.87 are present at significant levels, while level of the impurity RRT0.89 is below the ICH identification threshold. The structures of RRT=0.81 and RRT=0.87 were determined and are provided in Table 9. They hereby referred to as Impurity I and Impurity II, respectively.

TABLE 9

Structures of Impurities

| Code Name | Structural Formula |
|---|---|
| Impurity I (RRT 0.81) | 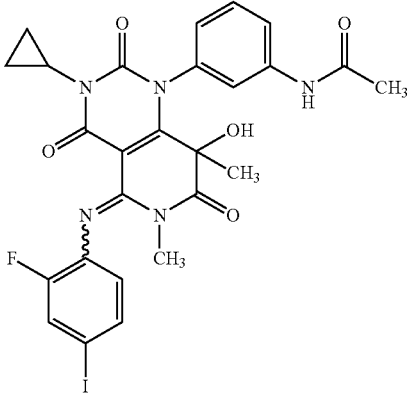 [SMILES: CC(=O)Nc1cccc(-n2c3c(c(=O)n(C4CC4)c2=O)C(=Nc2ccc(I)cc2F)N(C)C(=O)C3(C)O)c1] |
| Impurity II (RRT 0.87) | 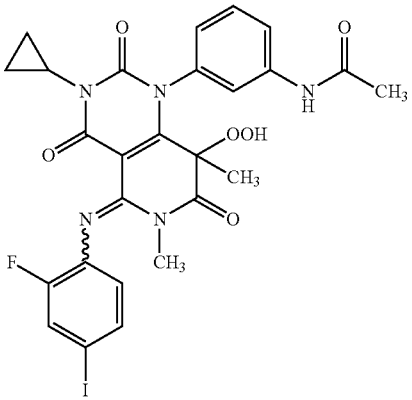 |
| RRT 0.89 | Structure is not determined |

In view of the results depicted in Tables 6, 7 and 8, the color in the tablet coating appears to play an important role in protecting Compound A from light degradation. The color coatings may prevent light induced impurities from being formed either by physically blocking the damaging wavelength or by providing chemical protection (scavenging oxidizing radicals).

As both pink and yellow Opadry® colors contained iron oxide and the Opadry® white did not; film coatings with a color containing iron oxide are anticipated to prevent light induced impurities in tablets containing Compound A.

As an alternative to film coatings containing a colorant (not white), uncoated tablets, wax coated tablets, white coated tablets and the like, can be placed in a protective light resistant blister pack or light resistant bottle to keep the drug away from light.

Particle Size

The benefit of drug substance micronization and use of specified disintegrants to improve the exposure was confirmed with a pre-clinical DMPK study. The variability of the pre-clinical exposure data using un-micronized drug substance suspended in 0.5% methyl cellulose ("un-micronized" in Table 10 below) was deemed unacceptable (both within and between studies). To test whether the variability in the exposure was due to variability in uniformity of the dose as well as the surface area of the suspended solids, an experiment was performed to determine the physical stability of suspensions made with un-micronized and micronized drug substance; and with and without specified disintegrants. The results of this experiment suggested that in order to ensure adequate reproducibility of the suspension dose it is necessary to use micronized drug substance. Suitably, the micronized drug substance is used with a specified disintegrant or specified disintegrants. The suspension made from un-micronized drug substance and without a specified disintegrant, showed rapid sedimentation and increase in particle size.

A suspension formulation was prepared from micronized drug substance suspended in a vehicle consisting of 5% mannitol, 1.5% hypromellose and 0.2% sodium lauryl sulfate ("micronized" in Table 10 below). Two concentrations were prepared: 26.9 mcg/mL and 134.4 mcg/mL and dosed the same day. On the third day the 134.4 mcg/mL suspension was dosed again along with a freshly prepared suspension of similar concentration Table 10 summarizes the exposure data (AUC) and FIG. 1 represents the results of the pre-clinical studies.

TABLE 10

Exposure in Pre-clinical Rat Studies

| | Area under the Curve (ng × hr/ml) - Mean (S.D.) or [Range] Dose (mg/m$^2$) | | | | | |
|---|---|---|---|---|---|---|
| Formulation | 1 | 3 | 5 | 10 | 20 | 30 |
| un-micronized[1] | | | | 102 [69-140] | | |
| un-micronized[1] | | | | 311 [296-333] | 1081 [576-1352] | 505 [397-628] |
| micronized C[2] | Day 1 | 140 (14) | 1712 (158) | | | |
| | Day 3 | | 1646 (403) | | | |
| | Day 3 NB | | 1888 (340) | | | |

NB = New batch of suspension.
[1]Un-micronized drug substance suspended in 0.5% Methylcellulose
[2]Micronized drug substance suspended in 1.5% hypromellose, 0.2% sodium lauryl sulfate, 5% mannitol FIG. 1—Exposure Data for Compound a in Pre-Clinical Studies.

The data in Table 10 and FIG. 1 indicate that both the mean exposure and reproducibility were significantly improved by using the micronized suspension, made form micronized drug substance. Suitably, the micronized drug substance is in a formulation with a specified disintegrant or specified disintegrants, suitably selected from one or more of: sodium lauryl sulfate, colloidal silicon dioxide and croscarmellose sodium.

By the term micronized, as used herein, is meant the standard usage in the art that the drug particles are processed, for example by milling, bashing and/or grinding, to significantly reduce particle size over those produced naturally during chemical synthesis. Suitably for use herein, at least 50% of the subject particles are 30 micron or less, suitably at least 50% of the particles are 10 micron or less, suitably at least 50% of the particles are 5 micron or less.

A suitable particle size distribution for the drug particles of the invention are as follows.
X10: NLT 0.46 μm
X50: 1.0-4.2 μm
X90: NMT 10.6 μm In one embodiment of the present invention, it was discovered that wet granulation or a tabletting technique that uses a significant water concentration is unsuitable for preparing tablets of Compound A, particularly on a commercial scale, because upon contact with water during the formulation process, Compound A can revert to Compound B which is significantly less soluble. Experiments were undertaken to determine the acceptable level of the desolvated Compound B in a pharmaceutical dosage form and the appropriate formulation techniques.

Desolvation

DMSO Content by HPLC

A gradient elution HPLC method was used to determine the DMSO content in Tablets containing Compound A. The typical chromatographic conditions are summarized in Table 11.

TABLE 11

Typical DMSO Content HPLC Instrument/Chromatographic Conditions

| Analytical Column Details (Type, particle size and dimensions) | Atlantis T3, 250 × 4.6 mm, 5 μm (or validated alternative) |
|---|---|
| Column Temperature | 40° C. |
| Mobile phase A | 100% Water |
| Mobile phase B | 100% Acetonitrile |
| Flow rate | 1.0 mL/min |
| Detector wavelength | UV at 195 nm |

| Content and Impurities Assay | | |
|---|---|---|
| | Time (min) | % A | % B |
| Gradient Profile | 0.0 | 100 | 0 |
| | 6.0 | 100 | 0 |
| | 7.0 | 20 | 80 |
| | 10.0 | 20 | 80 |
| | 10.1 | 100 | 0 |
| | 30.0 | 100 | 0 |
| Injection volume | 5 μL | | |
| Data collection time/reporting time | 10 min | | |
| Run Time | 30 minutes | | |

Figure 2:
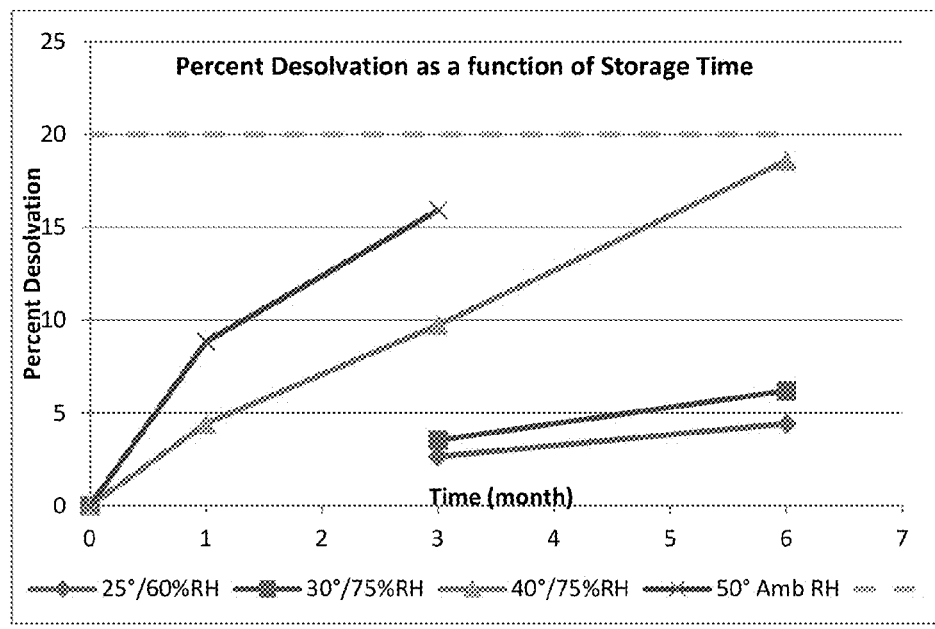
FIG. 2 depicts stability data for 1 mg tablets containing Compound A exposed to four different storage conditions.

Stability data for 1 mg tablets containing Compound A, made generally according to Example 2, exposed to four different storage conditions (30's count in HDPE Bottles with Desiccant) is presented in Table 12 and FIG. 2.

TABLE 12

| Storage Condition | Time (Months) | Content (% Label Claim) | DMSO Content (% of Compound A) | % Desolvation (Calculated)* | Dissolution (% released) Mean (min-max) |
|---|---|---|---|---|---|
| Specification | | 90.0-110.0% | 9.0-13.5 | NMT 20% | Complies with USP Q = 75% at 30 min. |
| Initial | 0 | 99.1 | 11.3 | 0 | 95 (92-98) |
| 25° C./60% RH | 3 | 98.8 | 11.0 | 2.65 | 97 (93-101) |
| | 6 | 100.6 | 10.8 | 4.42 | 92 (90-95) |
| 30° C./75% RH | 3 | 98.5 | 10.9 | 3.54 | 91 (85-98) |
| | 6 | 99.9 | 10.6 | 6.19 | 95 (91-100) |
| 40° C./75% RH | 1 | 98.7 | 10.8 | 4.42 | 94 (91-98) |
| | 3 | 99.3 | 10.2 | 9.73 | 94 (89-99) |
| | 6 | 100.6 | 9.2 | 18.58 | 93 (90-96) |
| 50° C. (ambient) | 1 | 99.3 | 10.3 | 8.85 | 94 (90-97) |
| | 3 | 99.8 | 9.5 | 15.93 | 96 (93-100) |

$$\% \text{ desolvation} = \frac{(\text{Initial DMSO content} - \text{current DMSO content}) \times 100}{\text{Initial DMSO content}}$$

FIG. 2—Stability Data for 1 Mg Tablets Containing Compound A

Extrapolated results show that the DMSO content lower limit corresponds to about 20% desolvation. Initial DMSO content corresponded to about 0%. Suitably, the initial DMSO content will be less than about 2% desolvation, suitably less than about 4% desolvation, suitably less than about 8% desolvation. Suitably, the DMSO content will not be less than an equivalent of about 5% desolvation during the shelf life of the tablet, suitably about 10% desolvation suitably about 15% desolvation, suitably about 20% desolvation. Consequently, dry direct compression and dry granulation were found to be appropriate formulation techniques.

The solid oral pharmaceutical dosage forms, suitably tablets, suitably capsules, of the present invention will typically be sized up to 1 gram, suitably from about 140 mg to about 175 mg. These solid dosage forms will contain Compound A in an amount selected from: 0.5 mg, 1 mg and 2 mg, by weight of Compound B. Tablet formulations of the invention may have a variety of shapes, including: round, modified round, diamond, modified capsule, modified oval, oval and hexagonal, and may optionally have a tilt.

Tablets

The choice of particular types and amounts of excipients, and tabletting technique employed depends on the further properties of Compound A and the excipients, e.g., compressibility, flowability, particle size, compatibility, and density. The tablets may be prepared according to methods known in the art, including dry direct compression and dry granulation, and the type of excipients used will vary depending on the exact process employed. It has been found that dry direct compression is particularly suitable for providing high strength, low breakage tablets comprising relatively low concentrations of Compound A (e.g., less than about 1.5%, suitably less than 1%), on a scale suitable for commercial production. Suitable dry direct compression tablets of the invention comprise dry blend comprising Compound A and one or more of fillers, binders and disintegrants, mixed with additional filler, binder, disintegrant and/or lubricant to form a compression mixture that is compressed to form tablets.

Included in the present invention are pharmaceutical compositions in tablet form, suitably prepared on a commercial scale, that comprise Compound A, wherein the tablet is made by a dry direct compression process using a diluent or diluents that are substantially free water. Also included in the present invention are such pharmaceutical compositions that contain a film coat, wherein the film coat contains a colored pigment.

Also included in the present invention are pharmaceutical compositions that comprise Compound A, wherein the tablet is made by a dry direct compression process, suitably on a commercial scale, using a diluent or diluents that are substantially free water and the Compound A particles are micronized.

The micronization of compound A enhances the biological exposure by increasing the particle specific surface area, as well as providing adequate content uniformity of the low strength solid dosage form.

Additionally, the use of a surfactant as disclosed herein further enhances the biological exposure by increasing the wettability of the micronized compound A.

In one embodiment of the present invention, the tablets of the present invention comprise:
(i) from about 0.3% to 1.5% Compound A;
(ii) from about 25% to about 89% of diluent;
(iii) up to about 8% binder, suitably up to about 5%;
(iv) up to about 2% lubricant, suitably up to about 0.75%;
(v) from 2% to about 8% disintegrant, suitably 3%;

In the foregoing embodiments, the diluent is suitably a combination of mannitol and microcrystalline cellulose, the binder is suitably HPMC, the lubricant is suitably magnesium stearate, and the disintegrant is suitably a combination of sodium lauryl sulfate, colloidal silicon dioxide and croscarmellose sodium.

In one embodiment of the current invention, tablets are coated with a film coat formed from an aqueous film coat composition. Aqueous film coat compositions suitable for use in the present invention comprise a film-forming polymer, water as a vehicle, and optionally one or more adjuvants such as are known in the film-coating art. Suitably, the film coat will contain a colored pigment.

Suitably, the colored pigment contains iron oxide.

The film-forming polymer is selected to form coatings with mechanical properties (e.g., mechanical strength, flexibility)

suitable to meet performance requirements, such as those required by the intended use environment (e.g., dissolution profile in gastrointestinal fluids), and/or use (e.g. solution viscosity). Examples of suitable film-forming polymers include cellulosic polymers (e.g., cellulose ethers such as HPMC, HPC, MC, EC, HEC, CAP, sodium ethyl cellulose sulfate, carboxymethyl cellulose and the like); polyvinylpyrolidone; zein; and acrylic polymers (e.g., methacrylic acid/ methacrylic acid ester copolymers such as methacrylic acid/ methylmethacrylate copolymers and the like). Cellulosic polymers are preferred in the present invention, especially cellulosic ethers and more especially HPMC and HPC. The polymers are typically provided in either aqueous or organic solvent based solutions or aqueous dispersions. However, the polymers may be provided in dry form, alone or in a powdery mixture with other components (e.g., a plasticizer and/or colorant), which is made into a solution or dispersion by the user by admixing with the aqueous vehicle.

The aqueous film coat composition further comprises water as a vehicle for the other components, to facilitate their delivery to the tablet surface. The vehicle may optionally further comprise one or more water soluble solvents, e.g., alcohols (e.g., methanol, isopropanol, propanol) and ketones (e.g., acetone). The skilled artisan can select appropriate vehicle components to provide good interaction between the film-forming polymer and the vehicle to ensure good film properties. In general, polymer-vehicle interaction is designed to yield maximum polymer chain extension to produce films having the greatest cohesive strength and thus mechanical properties. The components are also selected to provide good deposition of the film-forming polymer onto the tablet surface, such that a coherent and adherent film is achieved.

The aqueous film coating composition may optionally comprise one or more adjuvants known in the art, such as plasticizers, colorants, detackifiers, secondary film-forming polymers, flow aids, surfactants (e.g., to assist spreading), maltodextrin, and polydextrose.

Plasticizers provide flexibility to the film, which may reduce film cracking and improve adhesion to the tablet. Suitable plasticizers will generally have a high degree of compatibility with the film-forming polymer and sufficient permanence such that the coating properties are generally stable. Examples of suitable plasticizers include glycerin, propylene glycol, polyethylene glycols (e.g., molecular weight from 200 to 20,000, including Union Carbide's PEG 400, 4000, 6000, 8000, and 20,000), glycerin triacetate (aka triacetin), acetylated monoglyceride, citrate esters (e.g., triethyl citrate, acetyl triethyl citrate, tributyl citrate, acetyl tributyl citrate), phthalate esters (e.g., diethyl phthalate), mineral oil and hydrogenated glucose syrup. In one embodiment of the present invention, the plasticizer is chosen from polyethylene glycols, triacetin, propylene glycol, glycerin, and mixtures thereof.

Compound A was found to be sensitive to photo-induced degradation. A film coating, suitably a colored film coating, is advantageous to improve stability.

The aqueous film coat composition will typically comprise from about 5% to about 25%, suitably about 5% to about 20%, coating solids in the vehicle. In suitable embodiments, the solids typically comprise from about 25% to about 70%, suitably about 60% to about 70% film-forming polymer, about 5% to about 10%, suitably about 6% to about 8%, plasticizer, and about 20% to about 35% pigment and colorant, by weight. In suitable embodiments, the colorant comprises from about 0.5 to 3% by weight.

A number of suitable aqueous film coating compositions are commercially available. The aqueous film coat composition may be provided in the form of a solution or dispersion. Alternatively, the composition may be provided in a dry form that can be combined with the vehicle components according to supplier instructions prior to coating the tablet. Suitably, aqueous film coating compositions are those commercially available from Colorcon, Inc. of West Point, Pa., under the trade name OPADRY and OPADRY II (nonlimiting examples include Opadry Pink YS-1-14762-A or 03B140009, Opadry Yellow YS-1-12525-A or 03B120006). These compositions are available as dry film coating compositions that can be diluted in water shortly before use.

The tablets are also suitably coated to provide a uniform coating without speckling. The tablets are typically coated to provide a dry tablet weight gain of from about 2 to about 5%, suitably about 2.5 to 4%.

The uncoated tablet cores are coated with the aqueous film coating composition by methods well known in the art using commercially available equipment (e.g., Thomas Accela-Cota, Vector Hi-Coater, Compu-Lab 36). In general, the process usually involves rolling or tumbling the tablets in a pan, or suspending the tablets on a cushion of air (fluidized bed), and intermittently or continuously (preferably continuously) spraying a fine mist of atomized droplets of the coating composition onto the tablets, the droplets wetting, spreading and coalescing on the surface of the tablets to form an adherent and coherent film coating. The tablets are typically heated to about 40 to 50° C., suitably about 45 to 50° C., e.g., by air having a temperature of up to about 85° C., suitably about 65 to 80° C.

The invented solid oral pharmaceutical dosage forms may be administered in therapeutically effective amounts to treat or prevent a disease state, e.g., as described in the above referenced International Application No. PCT/JP2005/011082, and United States Patent Publication No. US 2006/0014768.

A method of this invention of inhibiting MEK activity in humans comprises administering to a subject in need of such activity a therapeutically effective amount of a solid oral pharmaceutical dosage form of the present invention.

The invention also provides for the use of Compound A in the manufacture of a solid oral pharmaceutical dosage form of the present invention.

The invention also provides for the use of Compound A in the manufacture of a solid oral pharmaceutical dosage form of the present invention for use in treating cancer.

The invention also provides for the use of Compound A in the manufacture of a solid oral pharmaceutical dosage form of the present invention for use in inhibiting MEK.

The invention also provides for a solid oral pharmaceutical dosage form for use as a MEK inhibitor which comprises Compound A and a pharmaceutically acceptable carrier of the present invention.

The invention also provides for a solid oral pharmaceutical dosage form for use in the treatment of cancer which comprises Compound A and a pharmaceutically acceptable carrier of the present invention.

The invention also provides for a solid oral pharmaceutical dosage form for use in inhibition MEK which comprises Compound A and a pharmaceutically acceptable carrier of the present invention.

Without further elaboration, it is believed that one skilled in the art can, using the preceding description, utilize the present invention to its fullest extent. The following Examples, therefore, are to be construed as merely illustrative and not a limitation of the scope of the present invention.

All the excipients utilized herein are standard pharmaceutical grade excipients available from numerous manufacturers well known to those in the art.

EXAMPLES

Examples 1 to 3

Tablet Preparation

Dry direct compression, tablets comprising Compound A and the ingredients in Table 13 were prepared.

TABLE 13

| | Strength (mg, as Compound B) | | |
|---|---|---|---|
| Component | 0.5 | 1 | 2 |
| Compound A, micronized[1] | 0.5635 | 1.127 | 2.254 |
| Sodium Lauryl Sulfate | 0.017 | 0.034 | 0.068 |
| Colloidal Silicon Dioxide | 0.010 | 0.020 | 0.040 |
| Mannitol | 95.47 | 101.509 | 106.95 |
| Microcrystalline Cellulose | 36.25 | 38.75 | 41.25 |
| Hypromellose | 7.25 | 7.75 | 8.25 |
| Croscarmellose Sodium | 4.35 | 4.65 | 4.95 |
| Magnesium Stearate | 1.09 | 1.16 | 1.24 |
| Opadry Pink YS-1-14762-A | NP | NP | 4.95 |
| Opadry Yellow YS-1-12525-A | 4.35 | NP | NP |
| Opadry White OY-S-28876 | NP | 4.65 | NP |
| Purified Water[2] | — | — | — |
| Total Tablet Weight | 149.35 | 159.65 | 169.95 |

Note:
[1]The amount of Compound A required to achieve the label claim of Compound B (the free or un-solvated compound) is calculated utilizing the molecular conversion factor of 0.8873 for the ratio of Compound B (un-solvated) to compound A (the DMSO solvate), and based on the purity value from the certificate of analysis. The amount of Mannitol is adjusted accordingly.
[2]Water is removed during processing.
NP = not present in formulation.

Blending

The micronized drug substance, sodium lauryl sulfate, silicon dioxide, croscarmellose sodium, microcrystalline cellulose and hypromellose are screened, if required, and transferred into a suitable bin blender and blended. The magnesium stearate is screened, if required, transferred to the bin blender and blended for an additional time.

Compression

The lubricated blend is compressed on a rotary tablet press to the target weight for each strength (145 mg, 155 mg and 165 mg corresponding to 0.5 mg, 1 mg and 2 mg, respectively). The compressed tablets are sampled for in-process monitoring of individual weight variation, appearance, hardness, thickness, friability and disintegration time.

Coating

Tablet cores are sprayed with an aqueous suspension of Opadry® Pink YS-1-14762-A) (for 2 mg strength), Opadry® Yellow YS-1-12525-A (for 0.5 mg strength) or Opadry® White OY-S-28876 (for 1 mg strength). Coating continues until a target weight gain of approximately 3% is attained. The tablets are then dried and bulk packed into HDPE containers with plastic liners and desiccant bags, and stored until packaged.

While the preferred embodiments of the invention are illustrated by the above, it is to be understood that the invention is not limited to the precise instructions herein disclosed and that the right to all modifications corning within the scope of the following claims is reserved.

What is claimed is:

1. A pharmaceutical tablet comprising:
   a) an amount of a drug, which is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, selected from: about 0.5635 mg, about 1.127 mg, and about 2.254 mg;
   wherein,
   b) the drug particles are micronized.

2. The pharmaceutical tablet, according to claim 1, comprising:
   a) an amount of a drug, which is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, selected from: about 0.5635 mg, about 1.127 mg, and about 2.254 mg;
   wherein,
   b) the drug particles are micronized; and
   c) the tablet contains from about 25% to about 89% by weight of one or more diluents, where the diluents are substantially free of water.

3. The pharmaceutical tablet, according to claim 1, comprising:
   a) an amount of a drug, which is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, selected from: about 0.5635 mg, about 1.127 mg, and about 2.254 mg;
   wherein,
   b) the drug particles are micronized; and
   c) the tablet contains from about 25% to about 89% by weight of one or more diluents selected from: microcrystalline cellulose, powdered cellulose, pregelatinized starch, starch, lactose, Di-calcium phosphate, lactitol, mannitol, sorbitol and maltodextrin, where the diluents are substantially free of water.

4. The pharmaceutical tablet, according to claim 1, comprising:
   a) an amount of a drug, which is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, selected from: about 0.5635 mg, about 1.127 mg, and about 2.254 mg;
   wherein,
   b) the drug particles are micronized;
   c) the tablet contains from about 25% to about 89% by weight of one or more diluents selected from: microcrystalline cellulose, powdered cellulose, pregelatinized starch, starch, lactose, Di-calcium phosphate, lactitol, mannitol, sorbitol and maltodextrin, where the diluents are substantially free of water; and
   d) the tablet is film coated.

5. The pharmaceutical tablet, according to claim 1, comprising:
   a) an amount of a drug, which is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, selected from: about 0.5635 mg, about 1.127 mg, and about 2.254 mg;

wherein,
b) the drug particles are micronized;
c) the tablet is produced on a scale suitable to prepare at least about 50,000 tablets;
d) the tablet contains from about 25% to about 89% by weight of one or more diluents selected from: microcrystalline cellulose, powdered cellulose, pregelatinized starch, starch, lactose, Di-calcium phosphate, lactitol, mannitol, sorbitol and maltodextrin, where the diluents are substantially free of water; and
e) the tablet is film coated.

6. The pharmaceutical tablet, according to claim 1, comprising:
a) an amount of a drug, which is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, selected from: about 0.5635 mg, about 1.127 mg, and about 2.254 mg;
wherein,
b) the drug particles are micronized;
c) the tablet is produced on a scale suitable to prepare at least about 50,000 tablets;
d) the tablet contains from about 25% to about 89% by weight of one or more diluents selected from: microcrystalline cellulose, powdered cellulose, pregelatinized starch, starch, lactose, Di-calcium phosphate, lactitol, mannitol, sorbitol and maltodextrin, where the diluents are substantially free of water; and
e) the tablet is film coated and wherein the film coating contains a colorant.

7. The pharmaceutical tablet, according to claim 1, comprising:
a) an amount of a drug, which is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, selected from: about 0.5635 mg, about 1.127 mg, and about 2.254 mg;
wherein,
b) the drug particles are micronized;
c) the tablet is produced on a scale suitable to prepare at least about 50,000 tablets;
d) the tablet contains from about 25% to about 89% by weight of one or more diluents selected from: microcrystalline cellulose, powdered cellulose, pregelatinized starch, starch, lactose, Di-calcium phosphate, lactitol, mannitol, sorbitol and maltodextrin, where the diluents are substantially free of water;
e) the tablet is film coated and wherein the film coating contains a colorant that contains iron oxide; and
f) amount of unsolvated drug does not exceed about 20%.

8. The pharmaceutical tablet comprising:
a) an amount of a drug, which is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, selected from: about 0.5635 mg, about 1.127 mg, and about 2.254 mg;
wherein,
b) at least 50% of the drug particles have a particle size of 30 micron or less.

9. The pharmaceutical tablet, according to claim 8, comprising:
a) an amount of a drug, which is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, selected from: about 0.5635 mg, about 1.127 mg, and about 2.254 mg;
wherein,
b) at least 50% of the drug particles have a particle size of 30 micron or less; and
c) the tablet contains from about 25% to about 89% by weight of one or more diluents, where the diluents are substantially free of water.

10. The pharmaceutical tablet, according to claim 8, comprising:
a) an amount of a drug, which is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, selected from: about 0.5635 mg, about 1.127 mg, and about 2.254 mg;
wherein,
b) at least 50% of the drug particles have a particle size of 30 micron or less;
c) the tablet contains from about 25% to about 89% by weight of one or more diluents selected from: microcrystalline cellulose, powdered cellulose, pregelatinized starch, starch, lactose, Di-calcium phosphate, lactitol, mannitol, sorbitol and maltodextrin, where the diluents are substantially free of water.

11. The pharmaceutical tablet, according to claim 8, comprising:
a) an amount of a drug, which is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, selected from: about 0.5635 mg, about 1.127 mg, and about 2.254 mg;
wherein,
b) at least 50% of the drug particles have a particle size of 30 micron or less;
c) the tablet contains from about 25% to about 89% by weight of one or more diluents selected from: microcrystalline cellulose, powdered cellulose, pregelatinized starch, starch, lactose, Di-calcium phosphate, lactitol, mannitol, sorbitol and maltodextrin, where the diluents are substantially free of water; and
d) the tablet is film coated.

12. The pharmaceutical tablet, according to claim 8, comprising:
a) an amount of a drug, which is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, selected from: about 0.5635 mg, about 1.127 mg, and about 2.254 mg;
wherein,
b) at least 50% of the drug particles have a particle size of 30 micron or less;
c) the tablet is produced on a scale suitable to prepare at least about 50,000 tablets;
d) the tablet contains from about 25% to about 89% by weight of one or more diluents selected from: microcrystalline cellulose, powdered cellulose, pregelatinized starch, starch, lactose, Di-calcium phosphate, lactitol, mannitol, sorbitol and maltodextrin, where the diluents are substantially free of water; and
e) the tablet is film coated.

13. The pharmaceutical tablet, according to claim 8, comprising:
   a) an amount of a drug, which is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, selected from: about 0.5635 mg, about 1.127 mg, and about 2.254 mg;
   wherein,
   b) at least 50% of the drug particles have a particle size of 30 micron or less;
   c) the tablet is produced on a scale suitable to prepare at least about 50,000 tablets;
   d) the tablet contains from about 25% to about 89% by weight of one or more diluents selected from: microcrystalline cellulose, powdered cellulose, pregelatinized starch, starch, lactose, Di-calcium phosphate, lactitol, mannitol, sorbitol and maltodextrin, where the diluents are substantially free of water; and
   e) the tablet is film coated and wherein the film coating contains a colorant.

14. The pharmaceutical tablet, according to claim 8, comprising:
   a) an amount of a drug, which is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, selected from: about 0.5635 mg, about 1.127 mg, and about 2.254 mg;
   wherein,
   b) at least 50% of the drug particles have a particle size of 30 micron or less;
   c) the tablet is produced on a scale suitable to prepare at least about 50,000 tablets;
   d) the tablet contains from about 25% to about 89% by weight of one or more diluents selected from: microcrystalline cellulose, powdered cellulose, pregelatinized starch, starch, lactose, Di-calcium phosphate, lactitol, mannitol, sorbitol and maltodextrin, where the diluents are substantially free of water;
   e) the tablet is film coated and wherein the film coating contains a colorant that contains iron oxide; and
   f) amount of unsolvated drug does not exceed about 20%.

15. The pharmaceutical tablet according to claim 2 wherein:
   the tablet contains from about 25% to about 89% by weight of one or more diluents selected from: microcrystalline cellulose and mannitol.

16. The pharmaceutical tablet according to claim 9 wherein:
   the tablet contains from about 25% to about 89% by weight of one or more diluents selected from: microcrystalline cellulose and mannitol.

17. A process for preparing pharmaceutical tablets containing an amount of a drug, which is N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate, in an amount selected from: about 0.5635 mg, about 1.127 mg, and about 2.254 mg, which process comprises the steps of;
   admixing:
      N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxide solvate,
      one or more excipients, where the excipients are substantially free of water, and
      further excipients,
      to form a mixture; and
   compressing the mixture into tablets;
   provided:
   each tablet contains N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide dimethyl sulfoxidein solvate in an amount selected from: about 0.5635 mg, about 1.127 mg, and about 2.254 mg; and
   at least 50% of the drug particles have a particle size of 30 micron or less.

\* \* \* \* \*